(12) United States Patent
Cumming et al.

(10) Patent No.: US 7,294,636 B2
(45) Date of Patent: Nov. 13, 2007

(54) CHEMICAL COMPOUNDS

(75) Inventors: John Cumming, Macclesfield (GB); Alan Faull, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 35 days.

(21) Appl. No.: 10/556,023

(22) PCT Filed: May 6, 2004

(86) PCT No.: PCT/SE2004/000697

§ 371 (c)(1),
(2), (4) Date: Nov. 8, 2005

(87) PCT Pub. No.: WO2004/099178

PCT Pub. Date: Nov. 18, 2004

(65) Prior Publication Data

US 2007/0015788 A1    Jan. 18, 2007

(30) Foreign Application Priority Data

May 9, 2003    (SE)    ..................................... 0301369

(51) Int. Cl.
*A01N 43/42* (2006.01)
*A61K 31/44* (2006.01)
*C07D 451/02* (2006.01)
*C07D 211/32* (2006.01)
*C07D 401/00* (2006.01)

(52) U.S. Cl. ...................... 514/304; 514/321; 514/322; 514/326; 546/124; 546/199; 546/208; 546/210

(58) Field of Classification Search ................ 546/124, 546/199, 208, 210; 514/304, 321, 322, 326
See application file for complete search history.

(56) References Cited

U.S. PATENT DOCUMENTS

| 3,203,992 A | 8/1965 | Kunz et al. |
| 3,577,432 A | 5/1971 | Helsley et al. |
| 3,755,584 A | 8/1973 | Plotnikoff et al. |
| 3,818,017 A | 6/1974 | Janssen et al. |
| 3,894,030 A | 7/1975 | Janssen et al. |
| 4,029,801 A | 6/1977 | Cavalla et al. |
| 4,105,666 A | 8/1978 | Ward |
| 4,105,771 A | 8/1978 | Archibald et al. |
| 4,166,119 A | 8/1979 | Effland et al. |
| 4,246,267 A | 1/1981 | Vincent et al. |
| 4,264,613 A | 4/1981 | Regnier et al. |
| 4,338,323 A | 7/1982 | Regnier et al. |
| 4,367,232 A | 1/1983 | Boix-Igleasias et al. |
| 5,576,321 A | 11/1996 | Krushinski, Jr. et al. |
| 5,595,872 A | 1/1997 | Wetterau, II et al. |
| 5,614,523 A | 3/1997 | Audia et al. |
| 5,614,533 A | 3/1997 | Anderson et al. |
| 5,627,196 A | 5/1997 | Audia et al. |
| 5,688,960 A | 11/1997 | Shankar |
| 5,696,267 A | 12/1997 | Reichard et al. |
| 5,741,789 A | 4/1998 | Hibschman et al. |
| 5,789,402 A | 8/1998 | Audia et al. |
| 5,840,725 A | 11/1998 | Reichard et al. |
| 6,790,854 B2 | 9/2004 | Tsushima et al. |
| 6,958,350 B2 | 10/2005 | Brough et al. |
| 6,960,602 B2 | 11/2005 | Burrows et al. |
| 7,041,667 B1 | 5/2006 | Armour et al. |
| 7,192,973 B2 | 3/2007 | Tucker |
| 2002/0094989 A1 | 7/2002 | Hale et al. |
| 2004/0006081 A1 | 1/2004 | Burrows et al. |
| 2004/0110952 A1 | 6/2004 | Burrows et al. |
| 2004/0122049 A1 | 6/2004 | Burrows et al. |
| 2004/0266823 A1 | 12/2004 | Cumming et al. |
| 2005/0014788 A1 | 1/2005 | Cumming et al. |
| 2005/0171353 A1 | 8/2005 | Cumming |
| 2005/0250792 A1 | 11/2005 | Thom et al. |
| 2006/0052413 A1 | 3/2006 | Tucker |
| 2006/0069120 A1 | 3/2006 | Oldfield et al. |
| 2006/0189650 A1 | 8/2006 | Cumming et al. |

FOREIGN PATENT DOCUMENTS

| DE | 37 23 568 A1 | 1/1989 |
| DE | 197 03 131 A1 | 7/1998 |
| DE | 197 55 268 A1 | 6/1999 |
| EP | 0 077 427 | 4/1983 |
| EP | 0 095 454 | 11/1983 |
| EP | 0 128 007 | 12/1984 |
| EP | 0 228 893 | 7/1987 |
| EP | 0 235 463 | 9/1987 |
| EP | 0 290 958 | 11/1988 |
| EP | 0 354 568 A2 | 2/1990 |
| EP | 0 407 217 A1 | 1/1991 |
| EP | 0 445 862 B1 | 9/1991 |
| EP | 0 457 686 B1 | 11/1991 |

(Continued)

OTHER PUBLICATIONS

Hariharan et al., "Interferon-γ Upregulates CCR5 expression in cord and adult blood mononuclear phagocytes", Blood, 1999, vol. 93, pp. 1137-1144.*

(Continued)

*Primary Examiner*—Margaret D. Seaman
*Assistant Examiner*—Niloofar Rahmani
(74) *Attorney, Agent, or Firm*—Fish & Richardson P.C.

(57) ABSTRACT

Compounds of formula (I): compositions comprising them, processes for preparing them and their use in medical therapy (for example modulating CCR5 receptor activity in a warm blooded animal)

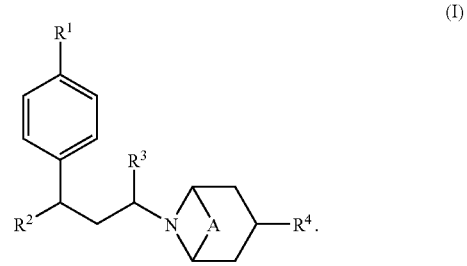

17 Claims, No Drawings

FOREIGN PATENT DOCUMENTS

| | | |
|---|---|---|
| EP | 0 496 691 A1 | 7/1992 |
| EP | 0 587 311 A1 | 3/1994 |
| EP | 0 625 507 B1 | 11/1994 |
| EP | 0 643 057 A1 | 3/1995 |
| EP | 0 722 941 A2 | 7/1996 |
| EP | 0 903 349 A2 | 3/1999 |
| EP | 1 013 276 A1 | 6/2000 |
| EP | 1 277 737 | 1/2003 |
| FR | 2 096 916 | 3/1972 |
| FR | 2 190 430 | 2/1974 |
| GB | 1368012 | 9/1974 |
| GB | 1 404 868 | 9/1975 |
| GB | 1425354 | 2/1976 |
| GB | 1 532 671 | 11/1978 |
| GB | 1 538 542 | 1/1979 |
| GB | 1 544 191 | 4/1979 |
| JP | 63264525 | 11/1988 |
| JP | 10259176 | 9/1998 |
| WO | WO 92/02502 | 2/1992 |
| WO | WO 92/15579 | 9/1992 |
| WO | WO 93/13083 | 7/1993 |
| WO | WO 93/15052 | 8/1993 |
| WO | WO 93/25528 | 12/1993 |
| WO | WO 94/27967 | 12/1994 |
| WO | WO 95/11880 | 5/1995 |
| WO | WO 96/19452 | 6/1996 |
| WO | WO 96/26205 | 8/1996 |
| WO | WO 96/34857 | 11/1996 |
| WO | WO 96/39386 | 12/1996 |
| WO | WO 97/10207 | 3/1997 |
| WO | WO 97/10212 | 3/1997 |
| WO | WO 97/19060 | 5/1997 |
| WO | WO 97/23458 | 7/1997 |
| WO | WO 97/42956 | 11/1997 |
| WO | WO 97/47299 | 12/1997 |
| WO | WO 98/02151 | 1/1998 |
| WO | WO 98/08826 | 3/1998 |
| WO | WO 98/31364 | 7/1998 |
| WO | WO 98/31366 | 7/1998 |
| WO | WO 98/32442 | 7/1998 |
| WO | WO 98/51311 | 11/1998 |
| WO | WO 99/04794 | 2/1999 |
| WO | WO 99/17773 | 4/1999 |
| WO | WO 99/25686 | 5/1999 |
| WO | WO 99/27928 | 6/1999 |
| WO | WO 99/27929 | 6/1999 |
| WO | WO 99/28314 | 6/1999 |
| WO | WO 99/31092 | 6/1999 |
| WO | WO 99/37304 | 7/1999 |
| WO | WO 99/37619 | 7/1999 |
| WO | WO 99/38514 | 8/1999 |
| WO | WO 99/64394 | 12/1999 |
| WO | WO 99/65895 | 12/1999 |
| WO | WO 00/08013 | 2/2000 |
| WO | WO 00/21948 | 4/2000 |
| WO | WO 00/21952 | 4/2000 |
| WO | WO 00/23076 | 4/2000 |
| WO | WO 00/35449 | 6/2000 |
| WO | WO 00/35451 | 6/2000 |
| WO | WO 00/39108 | 7/2000 |
| WO | WO 00/53600 | 9/2000 |
| WO | WO 00/58305 | 10/2000 |
| WO | WO 00/61559 | 10/2000 |
| WO | WO 00/69820 | 11/2000 |
| WO | WO 00/76511 | 12/2000 |
| WO | WO 00/76512 | 12/2000 |
| WO | WO 00/76513 | 12/2000 |
| WO | WO 00/76514 | 12/2000 |
| WO | WO 00/76972 | 12/2000 |
| WO | WO 00/76973 | 12/2000 |
| WO | WO 01/14333 | 3/2001 |
| WO | WO 01/19817 | 3/2001 |
| WO | WO 01/43744 | 6/2001 |
| WO | WO 01/44227 | 6/2001 |
| WO | WO 01/66525 | 9/2001 |
| WO | WO 01/87839 | 11/2001 |
| WO | WO 01/90106 | 11/2001 |
| WO | WO 01/92227 | 12/2001 |
| WO | WO 02/066460 | 8/2002 |
| WO | WO 02/070479 | 9/2002 |
| WO | WO 02/076948 | 10/2002 |
| WO | WO 02/079156 | 10/2002 |
| WO | WO 03/030898 | 4/2003 |
| WO | WO 03/042177 | 5/2003 |
| WO | WO 03/042178 | 5/2003 |
| WO | WO 03/042205 | 5/2003 |
| WO | WO 03/080574 | 10/2003 |
| WO | WO 2004/056773 | 7/2004 |
| WO | WO 2004/056808 | 7/2004 |
| WO | WO 2004/056809 | 7/2004 |

OTHER PUBLICATIONS

Balashov et al., "CCR5+ and CXCR3+ T cells are increased in multiple sclerosis and their ligands MIP-1α and IP-10 are expressed in demyelinating brain lesions", Proc. Natl. Acad. Sci., 1999, vol. 96, pp. 6873-6878.*

Zhang et al., "Synthesis and biological evaluation of tropane-like 1-{2-[Bis(bis(4-fluorophenyl)methoxy]ethyl}-4-(3-phenylpropyl)piperazine (GBR 12909) analogues", J. Med. Chem., vol. 44, 3937-3945, 2001.*

McGaw, "What it means when an examiner says 'election of species requirement'", Smith & Hopen Article ID:37 (2005), available online at http://www.smithhopen.com/faq_display.asp?faz_id=37.

Mensonides-Harsema et al., "Synthesis and in Vitro and in Vivo Functional Studies of Ortho-Substituted Phenylpiperazine and N-Substituted 4-N-(o-Methoxyphenyl)aminopiperidine Analogues of WAY100635", J. Med. Chem. 43:432-439 (2000).

Meurer et al., "Discovery of potent human CCR5 antagonists for the treatment of HIV-1 infection—II." CAPLUS 2000:331722 (2000).

Navas III et al., "The Design and Synthesis of a Hapten for 1192U90, A Potential Atypical Antipsychotic Agent", Synthetic Communications 26(7):1411-1421 (1996).

Naya et al., "Design, Synthesis, and Discovery of a Novel CCR1 Antagonist", J. Med. Chem. 44:1429-1435 (2001).

Ng et al., "Discovery of Novel Non-Peptide CCR1 Receptor Antagonists", J. Med. Chem. 42:4680-4694 (1999).

Patent Abstracts of Japan, Medicine Composition Containing Piperazine Derivative and Having Active Oxygen Production Inhibiting And Active Oxygen Removing Action (Nov. 1, 1988).

Payard et al., "N-Aminomethylated Derivatives of Some Hydroxamic Acids as Anti-Inflammatories", Eur. J. Med. Chem. pp. 1-10 (1975).

Rollins, "Chemokines", Blood 90(3):909-928 (1997).

Rubini et al., "Synthesis of Isosteric Methylene-Oxy Pseudodipeptide Analogues as Novel Amide Bond Surrogate Units", Tetrahedron 42(21):6039-6045 (1986).

Scott et al., "Secreted phospholipase A(2) enzymes as therapeutic targets", PubMed Abstract 12783578, also cited as Expert Opin Ther Targets 7(3):427-40 (2003).

Srulevitch et al., "4-Phenylamidopiperidines: synthesis, pharmacological testing and SAR analysis", Acta Pharm. Jugosl. 41:89-106 (1991).

Srulevitch et al., "Design, Synthesis and SAR of Analgesics", QSAR: Quantitative Structure-Activity Relationships in Drug Design, pp. 377-381 (1989).

Stefano et al., "Human neutrophil and macrophage chemokinesis induced by cardiopulmonary bypass: Loss of DAME and IL-1 chemotaxis", Journal of Neuroimmunology 47:189-198 (1993).

Timmermans et al., "Hypotensive Properties of Benzodioxane Derivatives Structurally Related to R28935. Comparison of Activity with some Receptor Affinities", Arch. Int. Pharmacodyn. 255:321-334 (1982).

Wade et al., "Application of Base Cleavable Safety Catch Linkers to Solid Phase Library Production", *J. Comb. Chem.* 2:266-275, see p. 269 scheme 3 and table 4, compounds 32 a-m (2000).

Wright et al., "Discovery of Selective Dopamine D4 Receptor Antagonists: 1-Aryloxy-3-(4-Aryloxypiperidinyl)-2-Propanols", *Bioorganic & Medicinal Chemistry Letters* 7(11):1377-1380 (1997).

Derwent Abstract 2000-339628/29 corresponding to PCT Application WO 00/23437 A1.

Derwent Abstract 96-136185/14 corresponding to Japanese Patent Application JP 08026999.

Derwent Abstract 96-136186/14 corresponding to Japanese Patent Application JP 08027000-A.

Derwent Abstract 96-136187/14 corresponding to Japanese Patent Application JP 08027001-A.

Derwent Abstract 97-212513/19, (2003), corresponding to Foreign Patent Document WO 97/10207, published Mar. 20, 1997 (Reference "ADDDD").

Derwent Abstract 98-351249/49, (2003), corresponding to Foreign Patent Document JP 63-264525, published Nov. 1, 1988 (Reference "AQQQ").

Derwent Abstract 99-040684/04 corresponding to Japanese Patent Application JP 10298180-A/2.

Emonds-Alt et al., "Pharmacological Profile and Chemical Synthesis of SR 48968, a Non-Peptide Antagonist of the Neurokinin A (NK$_2$) Receptor", *Bioorganic & Medicinal Chemistry Letters* 3(5):925-930 (1993).

Friebe et al., "Piperidinopropyl derivatives and pharmaceutical compositions containing them", *CAPLUS* 94:103172 (1981).

Gerard, "Chemokine Receptors and Ligand Specificity: Understanding the Enigma", *Contemp. Cancer Res.* 4 (Chemokines and Cancer) 21-31 (1999).

Granata et al., "Secretory phospholipases a(2) as multivalent mediators of inflammatory and allergic disorders", PubMed Abstract 12876405, also cited as *Int Arch Allergy Immunol.* 131(3):153-63 (2003).

Hesselgesser et al., "Identification and Characterization of Small Molecule Functional Antagonists of the CCR1 Chemokine Receptor", *J. Biol. Chem.* 273(25):15687-15692 (1998).

Howard et al., "Chemokines: progress toward identifying molecular targets for therapeutic agents", *Trends in Biotechnology* 14:46-51 (1996).

Janda, "A Soluble Polymer Approach to the "Fishing Out" Principle: Synthesis and Purification of β-Amino Alcohols", *J. Org. Chem.* 63:889-894 (1998).

Komai et al., "Structure-Activity Relationships of HIV-1 PR Inhibitors Containing AHPBA-II. Modification of Pyrrolidine Ring at P1 Proline", *Bioorganic & Medicinal Chemistry* 4(8):1365-1377 (1996).

Kraiss et al., "Chemistry of Tropan-3-yl Ethers. Part I. Synthesis of Tropan-3-yl Ethers", *J. Chem. Soc. (B) Phys. Org.* 2145-2149 (1971).

Lawrence et al., "Automated Synthesis and Purification of Amides: Exploitation of Automated Solid Phase Extraction in Organic Synthesis", *Synthesis* 553-558, see table 1, (May 1997).

Leclerc et al., "Derivatives Related to Betaxolol with α-and β-Adrenergic Activities", *Arzneim-Forsch/Drug. Res.* 35(11):1357-1367 (1985).

Lynch et al., "1,3,4-Trisubstituted Pyrrolidine CCR5 Receptor Antagonists: Modifications of the Arylpropylpiperidine Side Chains", *Bioorg. Med. Chem. Lett.* 13:119-123 (2003).

Archibald et al., "Antihypertensive Ureidopiperidines", *J. Med. Chem.* 23:857-861 (1980).

Archibald et al., "Antiinflammatory 4-acylaminopiperidines", *CAPLUS* 77:34355 (1972).

Berkoff et al., "The Reductive Decyanation of Nitriles by Alkali Fusion", *Synthetic Communications* 10(12):939-945 (1980).

CAPLUS accession No. 1978:22640, document No. 88:22640, Yoshitomi Pharmaceutical Industries Ltd.: "Urea and thiourea derivatives" & JP, A2, 52085174, 19770715.

CAPLUS accession No. 1990:558675, document No. 113:158675, Yoshitomi Pharmaceutical Industries, Ltd.: "Dihydroxycinnamic acid amide derivatives and their pharmaceutical compositions for enhancement of nerve growth factor (NGF) production"& JP, A2, 02104568, 19900417.

CASREACT accession No. 112:216654, Inst. Pharm. Chem.: "Sodium mercury EDTA dehydrogenation of N-aliphatic-substituted 1,2,3,6-tetrahydropyridine derivatives", *Archiv der Pharmazie* 323(2):109-115 (1990).

CASREACT accession No. 96:199236, Chem. Dep., Glaxo Group Res. Ltd., "Arylethanolamines derived from salicylamine with α- and β-adrenoceptor blocking activities. Preparation of labetalol, its enantiomers and related salicylamides", *J. Med. Chem.* 25(6):670-679 (1982).

Caltanach et al., "Studies in the Indole Series Part IV Tetrahydro-1*H*-pyrido[4,3-b]-indoles as Serotonin Antagonists", *J. Chem. Soc. (C)* 10:1235-1243 (1968).

Cohen et al., "Cytokine function: A study in biologic diversity", *CAPLUS* 125:31527 (1996).

Derwent Abstract 2000-587420/55, (2003), corresponding to Foreign Patent Document WO 00/53600, published Sep. 14, 2000 (Reference "AIIIII").

Derwent Abstract 54050W/33 corresponding to Belgium Application BE 826994.

* cited by examiner

CHEMICAL COMPOUNDS

CROSS-REFERENCE TO RELATED APPLICATIONS

This application is a national phase application under 35 U.S.C. § 371 of PCT International Application No. PCT/SE2004/000697, filed May 6. 2004, which claims priority to Swedish Application Serial No. 0301369-5, filed May 9, 2003.

The present invention relates to heterocyclic derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO01/87839, WO01/66525, WO00/08013, WO99/38514 and WO99/04794.

Chemokines are chemotactic cytokines that are released by a wide variety of cells to attract macrophages, T cells, eosinophils, basophils and neutrophils to sites of inflammation and also play a role in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β,).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES), macrophage inflammatory proteins (MIP) MIP-1α and MP-1β and monocyte chemoattractant protein-2 (MCP-2).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

The present invention provides a compound of formula (I):

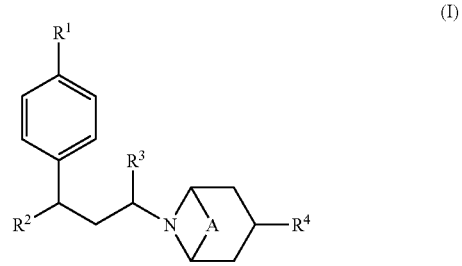

wherein:
A is absent or is $CH_2CH_2$;
$R^1$ is halo, hydroxy, nitro, $(CH_2)_nS(O)_k(C_{1-6}alkyl)$, $(CH_2)_nS(O)_2NH_2$, $(CH_2)_nS(O)_2NH(C_{1-6}$ alkyl), $(CH_2)_nS(O)_2NH$-CHO, $(CH_2)_nS(O)_2N(C_{1-6}$ alkyl$)_2$, $OS(O)_2(C_{1-6}$ alkyl), cyano, $C_{1-6}$alkyl, $C_{1-6}$ alkoxy, $NH_2$, $NH(C_{1-6}$ alkyl), $N(C_{1-6}$ alkyl$)_2$, $C(O)NH_2$, $C(O)NH(C_{1-6}$ alkyl), $C(O)N(C_{1-6}$ alkyl$)_2$, $C(O)$[N-linked heterocyclyl], $CO_2H$, $CO_2(C_{1-6}$ alkyl), $NHC(O)(C_{1-6}$ alkyl), $NHC(O)O(C_{1-6}$ alkyl), $(CH_2)_nNHS(O)_2(C_{1-6}$ alkyl), $C(O)(C_{1-6}$ alkyl), $CF_3$, $OCF_3$, phenyl, heteroaryl, $(C_{1-4}$ alkyl)phenyl, $(C_{1-4}$ alkyl)heteroaryl, NHC(O)phenyl, NHC(O)heteroaryl, $NHC(O)(C_{1-4}$ alkyl)phenyl, $NHC(O)(C_{1-4}$ alkyl)heteroaryl, $NHS(O)_2$phenyl, $NHS(O)_2$heteroaryl, $NHS(O)_2(C_{1-4}$ alkyl)phenyl, $NHS(O)_2(C_{1-4}$ alkyl)heteroaryl, $NHC(O)NH(C_{1-6}$ alkyl), $NHC(O)NH(C_{3-7}$ cycloalkyl), NHC(O)NHphenyl, NHC(O)NHheteroaryl, $NHC(O)NH(C_{1-4}$ alkyl)phenyl or $NHC(O)NH(C_{1-4}$ alkyl)heteroaryl; wherein the foregoing phenyl and heteroaryl groups are optionally substituted by halo, hydroxy, nitro, $S(O)_m(C_{1-4}$ alkyl), $S(O)_2NH_2$, $S(O)_2NH(C_{1-4}$ alkyl), $S(O)_2N(C_{1-4}$ alkyl$)_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);
$R^2$ is phenyl, halophenyl, thienyl or halothienyl;
$R^3$ is hydrogen or methyl;
$R^4$ is a five membered heterocycle containing at least one carbon atom, one to four nitrogen atoms and, optionally, one oxygen or sulphur atom, said heterocycle being optionally substituted by oxo, $C_{1-6}$ alkyl, $H_2NC(O)$, (phenyl$C_{1-2}$ alkyl) HNC(O), $C_{1-2}$ alkyl(phenyl) [which is optionally substituted by halogen, $C_{1-4}$ alkyl, $C_{1-4}$alkoxy, $CF_3$, $OCF_3$, $S(C_{1-4}$ alkyl), $S(O)(C_{1-4}$ alkyl) or $S(O)_2(C_{1-4}$ alkyl)], $S(C_{1-4}$ alkyl), $S(C_{1-2}$ alkyl(phenyl)), $NH_2$ or phenyl; the five membered heterocycle being optionally fused to a cyclohexane, piperidine, benzene, pyridine, pyridazine, pyrimidine or pyrazine ring; the ring carbon atoms of said fused cyclohexane, piperidine, benzene, pyridine, pyridazine, pyrimidine or pyrazine ring being optionally substituted by halogen, cyano, $C_{1-4}$ alkyl, $C_{1-4}$alkoxy, $CF_3$, $OCF_3$, $NH_2$, $S(C_{1-4}$ alkyl), $S(O)(C_{1-4}$ alkyl) or $S(O)_2(C_{1-4}$ alkyl); and the nitrogen of the fused piperidine ring being optionally substituted by $C_{1-4}$ alkyl {which is optionally substituted by oxo, halogen, OH, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl$)_2$, $NH_2$, $NH(C_{1-4}$ alkyl) or $N(C_{1-4}$ alkyl$)_2$}, $C(O)(C_{1-4}$ alkyl) {wherein the alkyl is optionally substituted by $C_{1-4}$alkoxy or fluoro}, $C(O)O(C_{1-4}$ alkyl), $C(O)NH_2$, $C(O)NH(C_{1-4}$ alkyl), $C(O)$ N($C_{1-4}$ alkyl)$_2$ or S(O)$_2$($C_{1-4}$ alkyl) {wherein the alkyl is optionally substituted by fluoro};

k, m and n are, independently, 0, 1 or 2;

or a pharmaceutically acceptable salt thereof or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts (adducts) such as a hydrochloride, hydrobromide, phosphate, acetate, fumarate, maleate, tartrate, citrate, oxalate, methanesulphonate or p-toluenesulphonate, or, additionally, formate. Acid addition salt is, for example hydrochloride or formate.

The compounds of the invention may exist as solvates (such as hydrates) and the present invention covers all such solvates.

Halogen is, for example, chloro, fluoro or bromo; such as chloro or fluoro.

Alkyl groups and moieties are straight or branched chain and are, for example, methyl (sometimes abbreviated to Me), ethyl, n-propyl, iso-propyl, n-butyl, sec-butyl or tert-butyl.

Cycloalkyl is for example, cyclopropyl, cyclopentyl or cyclohexyl.

N-Linked heterocyclyl is a nitrogen-linked, non-aromatic 3, 4, 5 or 6 membered ring optionally comprising one further heteroatom (selected from the group comprising nitrogen, oxygen and sulphur). It is, for example, aziridinyl, azetidinyl, pyrrolidinyl, piperidinyl, piperazinyl, morpholinyl or thiomorpholinyl.

Heteroaryl is an aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heteroaryl is, for example, furyl, thienyl (also known as thiophenyl), pyrrolyl, thiazolyl, isothiazolyl, pyrazolyl, oxazolyl, isoxazolyl, imidazolyl, [1,2,4]-triazolyl, pyridinyl, pyrimidinyl, indolyl, benzo[b]furyl (also known as benzfuryl), benz[b]thienyl (also known as benzthienyl or benzthiophenyl), indazolyl, benzimidazolyl, benztriazolyl, benzoxazolyl, benzthiazolyl, 1,2,3-benzothiadiazolyl, an imidazopyridinyl (such as imidazo[1,2a]pyridinyl), thieno[3,2-b]pyridin-6-yl, 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, a pyrazolopyridine (for example 1H-pyrazolo[3,4-b]pyridinyl), quinolinyl, isoquinolinyl, a naphthyridinyl (for example [1,6]naphthyridinyl or [1,8]naphthyridinyl), a benzothiazinyl or dibenzothiophenyl (also known as dibenzothienyl); or an N-oxide thereof, or an S-oxide or S-dioxide thereof. Heteroaryl is especially pyridyl, pyrimidinyl, indolyl or benzimidazolyl.

The five membered heterocycle of $R^4$ is, for example, pyrazolyl, imidazolyl, 1,2,4-triazolyl, 1,2,3-triazolyl, tetrazolyl, oxazolyl, isoxazolyl, 1,2,4-oxadiazolyl, 1,3,4-oxadiazolyl or thiazolyl. When the five membered heterocycle of $R^4$ is fused to a benzene or pyridine ring the resulting bicyclic is, for example, benzimidazolyl, benztriazolyl or an imidazopyridinyl (such as imidazo[4,5-c]pyridinyl). When the five membered ring heterocycle of $R^4$ is fused to a saturated cycloalkyl or piperidine the resulting bicyclic is, for example, 4,5,6,7-tetrahydro-1H-benzimidazole, 4,5,6,7-tetrahydro-3H-imidazo[4,5-c]pyridine or 4,5,6,7-tetrahydro-1H-imidazo[4,5-c]pyridine. In one particular aspect of the invention the five membered ring heterocycle of $R^4$ is, for example, pyrazolyl, imidazolyl, 1,2,4-triazolyl, 1,2,3-triazolyl, tetrazolyl, oxazolyl, isoxazolyl, 1,2,4-oxadiazolyl or 1,3,4-oxadiazolyl. When the five membered ring heterocycle of $R^4$ is fused to a benzene ring the resulting bicyclic is, for example, benzimidazol-1-yl.

($C_{1-4}$ Alkyl)phenyl is, for example, benzyl, 2-phenylethyl or 1-phenyleth-1-yl. ($C_{1-4}$ Alkyl)heteroaryl is, for example, pyridylmethyl or pyrimidinylmethyl. NHC(O)Heteroaryl is, for example, NHC(O)pyridyl. NHC(O)($C_{1-4}$ Alkyl)phenyl is, for example, NHC(O)benzyl. NHC(O)($C_{1-4}$ Alkyl)heteroaryl is, for example, NHC(O)CH$_2$pyridyl. NHS(O)$_2$Heteroaryl is, for example, NHS(O)$_2$pyridyl. NHS(O)$_2$($C_{1-4}$ Alkyl)phenyl is, for example, NHS(O)$_2$benzyl. NHS(O)$_2$($C_{1-4}$ Alkyl)heteroaryl is, for example, NHS(O)$_2$CH$_2$pyridyl. NHC(O)NHheteroaryl is, for example, NHC(O)NHpyridyl. NHC(O)NH($C_{1-4}$ Alkyl)phenyl is, for example, NHC(O)NHbenzyl. NHC(O)NH($C_{1-4}$ Alkyl)heteroaryl is, for example, NHC(O)NHCH$_2$pyridyl.

In another aspect of the invention $R^4$ is a five membered ring aromatic heterocycle containing at least one carbon atom, one to four nitrogen atoms and, optionally, one oxygen atom, said heterocycle being optionally substituted by $C_{1-6}$ alkyl or benzyl [which is optionally substituted by halogen, $C_{1-4}$ alkyl, $C_{1-4}$alkoxy, CF$_3$, OCF$_3$, S($C_{1-4}$ alkyl) or S(O)$_2$($C_{1-4}$ alkyl)], and being optionally fused to a benzene ring, said fused benzene ring being optionally substituted by halogen, cyano, $C_{1-4}$ alkyl, $C_{1-4}$ alkoxy, CF$_3$, OCF$_3$, S($C_{1-4}$ alkyl) or S(O)$_2$($C_{1-4}$ alkyl).

In yet another aspect of the invention k and m are, independently, 0 or 2. In a further aspect of the invention k and m are both 2.

In another aspect of the invention A is absent.

In a further aspect of the invention n is 0.

In a still further aspect of the invention $R^1$ is halo, S(O)$_k$($C_{1-6}$ alkyl), OS(O)$_2$($C_{1-6}$ alkyl), S(O)$_2$NH$_2$, S(O)$_2$NH($C_{1-6}$ alkyl), S(O)$_2$N($C_{1-6}$ alkyl)$_2$, cyano, NH$_2$, NH($C_{1-6}$ alkyl), N($C_{1-6}$ alkyl)$_2$, CO$_2$($C_{1-6}$ alkyl), NHC(O)($C_{1-6}$ alkyl), NHC(O)O($C_{1-6}$ alkyl), NHS(O)$_2$($C_{1-6}$ alkyl), NHC(O)phenyl, NHC(O)heteroaryl, NHC(O)($C_{1-4}$ alkyl)phenyl, NHC(O)($C_{1-4}$ alkyl)heteroaryl, NHS(O)$_2$phenyl, NHS(O)$_2$heteroaryl, NHS(O)$_2$($C_{1-4}$ alkyl)phenyl, NHS(O)$_2$($C_{1-4}$ alkyl)heteroaryl, NHC(O)NH($C_{1-6}$ alkyl), NHC(O)NH($C_{3-7}$ cycloalkyl), NHC(O)NHphenyl, NHC(O)NHheteroaryl, NHC(O)NH($C_{1-4}$ alkyl)phenyl or NHC(O)NH($C_{1-4}$ alkyl)heteroaryl; wherein the foregoing phenyl and heteroaryl groups are optionally substituted by halo, hydroxy, nitro, S(O)$_m$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$, CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$; k and m are, independently, 0 or 2.

In a further aspect of the invention $R^1$ is halo, cyano, S(O)$_2$($C_{1-6}$ alkyl), OS(O)$_2$($C_{1-6}$ alkyl), CO$_2$($C_{1-6}$ alkyl), NHC(O)($C_{1-6}$ alkyl), NHS(O)$_2$($C_{1-6}$ alkyl), NHC(O)phenyl, NHC(O)heteroaryl, NHC(O)($C_{1-4}$ alkyl)phenyl, NHC(O)($C_{1-4}$ alkyl)heteroaryl, NHS(O)$_2$phenyl, NHS(O)$_2$heteroaryl, NHS(O)$_2$($C_{1-4}$ alkyl)phenyl or NHS(O)$_2$($C_{1-4}$ alkyl)heteroaryl; wherein the foregoing phenyl and heteroaryl groups are optionally substituted by halo, hydroxy, nitro, S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$, CO$_2$H, CO$_2$($C_{1-4}$ alkyl), NHC(O)($C_{1-4}$ alkyl), NHS(O)$_2$($C_{1-4}$ alkyl), C(O)($C_{1-4}$ alkyl), CF$_3$ or OCF$_3$.

In a still further aspect of the invention $R^1$ is halo, cyano, $S(O)_2(C_{1-6}$ alkyl), $OS(O)_2(C_{1-6}$ alkyl), $CO_2(C_{1-6}$ alkyl), $NHC(O)(C_{1-6}$ alkyl) or $NHS(O)_2(C_{1-6}$ alkyl).

In another aspect $R^1$ is $S(O)_k(C_{1-4}$ alkyl), wherein k is 0, 1 or 2, (for example $SCH_3$, $S(O)CH_3$ or $S(O)_2CH_3$), NHS $(O)_2(C_{1-4}$ alkyl) (for example $NHS(O)_2CH_3$) or $NHC(O)$ $(C_{1-4}$ alkyl) (for example $NHC(O)CH_3$). In yet another aspect $R^1$ is $S(O)_2(C_{1-4}$ alkyl) (for example $S(O)_2CH_3$), $NHS(O)_2(C_{1-4}$ alkyl) (for example $NHS(O)_2CH_3$) or $NHC(O)(C_{1-4}$ alkyl) (for example $NHC(O)CH_3$). In a still further aspect $R^1$ is $S(O)_2(C_{1-4}$ alkyl) (for example $S(O)_2CH_3$).

In a further aspect of the invention $R^2$ is phenyl, halophenyl (for example mono-chlorophenyl, mono-fluorophenyl or di-fluorophenyl; such as 3-fluorophenyl or 3,5-difluorophenyl), thienyl or halothienyl (for example mono-chlorothienyl; such as 4-chlorothien-2-yl or 5-chlorothien-2-yl). In a still further aspect $R^2$ is halophenyl (for example mono-chlorophenyl, mono-fluorophenyl or di-fluorophenyl; such as 3-fluorophenyl or 3,5-difluorophenyl). In another aspect $R^2$ is phenyl, halophenyl (for example mono-chlorophenyl, mono-fluorophenyl or di-fluorophenyl; such as 3-fluorophenyl or 3,5-difluorophenyl) or thienyl. In yet another aspect $R^2$ is 3-fluorophenyl or 3,5-difluorophenyl.

In a still further aspect $R^3$ is hydrogen.

In another aspect of the invention $R^4$ is other than an optionally substituted indolyl group.

In another aspect $R^4$ is imidazolyl, 1,2,4-triazolyl, 1,2,4-oxadiazolyl, tetrazolyl, pyrazolyl or 1,3-thiazolyl, isoxazolyl optionally substituted as described above.

In yet another aspect $R^4$ is 1,2,4-triazolyl, thiazolyl, 1,2,4-oxadiazolyl, imidazolyl or 1,2,3-triazolyl substituted as described above. In a further aspect $R^4$ is 1,2,4-triazolyl, thiazolyl, 1,2,4-oxadiazolyl, benzimidazolyl, benztriazolyl or an imidazopyridinyl (such as imidazo[4,5c]pyridinyl), each of which is unsubstituted or substituted by one or two of the same or different $C_{1-6}$ alkyl (for example $C_{1-4}$ alkyl; such as methyl), $CF_3$, OH (which may tautomerise to the keto form), $S(O)_2(C_{1-4}$ alkyl), $C(O)NH_2$, $C(O)NH(phenyl$ $(C_{1-2}$ alkyl)) or phenyl($C_{1-2}$ alkyl); wherein the phenyl of the foregoing phenyl($C_{1-2}$ alkyl) groups is optionally substituted by halo, $C_{1-4}$ alkyl, $C_{1-4}$alkoxy, cyano or $S(O)_2(C_{1-4}$ alkyl).

In a further aspect $R^4$ is pyrazolyl, 1,2,4-triazolyl, tetrazolyl, isoxazolyl or 1,2,4-oxadiazolyl, substituted as described above. In a further aspect $R^4$ is pyrazolyl, 1,2,4-triazolyl, tetrazolyl, isoxazolyl or 1,2,4-oxadiazolyl each of which is unsubstituted or substituted by one or two of the same or different $C_{1-6}$ alkyl. (for example $C_{1-4}$ alkyl; such as methyl, ethyl or iso-propyl) or benzyl (optionally substituted (for example unsubstituted or mono-substituted) by halogen, $S(C_{1-4}$ alkyl) or $S(O)_2(C_{1-4}$ alkyl)).

In a still further aspect $R^4$ is benzimidazolyl (for example benzimidazol-1-yl) which is optionally substituted on the benzene part (for example mono-substituted at the 5-position of the benzimidazolyl) by halogen, cyano, $C_{1-4}$ alkyl, $C_{1-4}$ alkoxy, $CF_3$, $OCF_3$, $S(C_{1-4}$ alkyl) or $S(O)_2(C_{1-4}$ alkyl). In another aspect $R^4$ is benzimidazolyl (for example benzimidazol-1-yl) which is optionally substituted on the benzene part (for example mono-substituted at the 5-position of the benzimidazolyl) by $S(O)_2(C_{1-4}$ alkyl).

In another aspect of the invention $R^4$ is imidazolyl, 1,2,4-triazolyl, 1,2,4-oxadiazolyl, tetrazolyl, pyrazolyl or 1,3-thiazolyl, said ring being optionally substituted by oxo, $C_{1-6}$ alkyl (such as methyl or iso-propyl), $C_{1-2}$ alkyl(phenyl) {wherein the phenyl is optionally substituted by halo (such as chloro or fluoro) or $S(O)_2(C_{1-4}$ alkyl) (such as $S(O)_2CH_3$}, $S(C_{1-4}$ alkyl) (such as $SCH_3$), $S(C_{1-2}$ alkyl(phenyl)) (such as $SCH_2C_6H_5$), $NH_2$ or phenyl; said ring optionally being fused to a benzene ring, said benzene ring being optionally substituted by cyano or $S(O)_2(C_{1-4}$ alkyl) (such as $S(O)_2CH_3$).

In yet another aspect the present invention provides a compound of formula (I) wherein A is absent or is $CH_2CH_2$; $R^1$ is $S(O)_2(C_{1-4}$ alkyl) (such as $S(O)_2CH_3$); $R^2$ is phenyl, halophenyl (such as 3-fluorophenyl, 3,5-difluorophenyl or 3-chloro-5-fluorophenyl), thienyl or halothienyl (such as 5-chlorothien-2-yl or 4-chlorothien-2-yl); $R^3$ is hydrogen; $R^4$ is imidazolyl, 1,2,4-triazolyl, 1,2,4-oxadiazolyl, tetrazolyl, pyrazolyl or 1,3-thiazolyl, said ring being optionally substituted by oxo, $C_{1-6}$ alkyl (such as methyl or iso-propyl), $C_{1-2}$ alkyl(phenyl) {wherein the phenyl is optionally substituted by halo (such as chloro or fluoro) or $S(O)_2(C_{1-4}$ alkyl) (such as $S(O)_2CH_3$}, $S(C_{1-4}$ alkyl) (such as $SCH_3$), $S(C_{1-2}$ alkyl(phenyl)) (such as $SCH_2C_6H_5$), $NH_2$ or phenyl; said ring optionally being fused to a benzene ring, said benzene ring being optionally substituted by cyano or $S(O)_2(C_{1-4}$ alkyl) (such as $S(O)_2CH_3$).

The compounds listed in Table I illustrate the invention. In another aspect the present invention provides each individual compound recited in Table I.

TABLE I

Table I comprises compounds of formula (I) wherein A is absent.

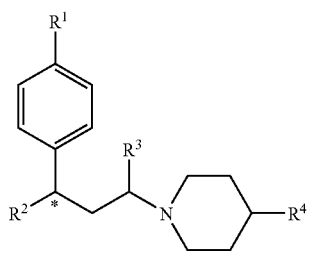

| Compound No. | $R^1$ | $R^2$ | $R^3$ | $R^4$ | *Chirality | Adduct | LCMS (MH+) |
|---|---|---|---|---|---|---|---|
| 1 | $CH_3S(O)_2$ | 3-Fluorophenyl | H | 5-$CH_3S(O)_2$-benzimidazol-1-yl | R isomer | — | 570 |
| 2 | $CH_3S(O)_2$ | 3-Fluorophenyl | H | 3-$CH_3$-5-$(CH_3)_2CH$-[1,2,4]triazol-4-yl | R isomer | — | 499 |
| 3 | $CH_3S(O)_2$ | Phenyl | H | 3-((4-$CH_3S(O)_2$-phenyl)$CH_2$)[1,2,4]-oxadiazol-5-yl | S isomer | hydrochloride | 594 |
| 4 | $CH_3S(O)_2$ | Phenyl | H | 3-(benzyl)[1,2,4]-oxadiazol-5-yl | S isomer | hydrochloride | 516 |

TABLE I-continued

Table I comprises compounds of formula (I) wherein A is absent.

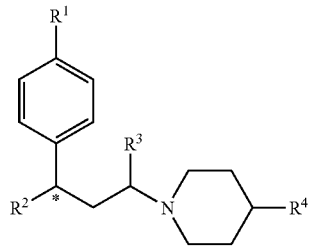

| Compound No. | $R^1$ | $R^2$ | $R^3$ | $R^4$ | *Chirality | Adduct | LCMS (MH+) |
|---|---|---|---|---|---|---|---|
| 5 | $CH_3S(O)_2$ | Phenyl | H | 5-$CH_3S(O)_2$-benzimidazol-1-yl | S isomer | — | 552 |
| 6 | $CH_3S(O)_2$ | Phenyl | H | 3-((4-$CH_3S$-phenyl)$CH_2$)[1,2,4]-oxadiazol-5-yl | S isomer | hydrochloride | 562 |
| 7 | $CH_3S(O)_2$ | Thien-3-yl | H | 5-$CH_3S(O)_2$-benzimidazol-1-yl | R isomer | — | 558 |
| 8 | $CH_3S(O)_2$ | Thien-2-yl | H | 5-$CH_3S(O)_2$-benzimidazol-1-yl | R isomer | — | 558 |
| 9 | $CH_3S(O)_2$ | 5-Chlorothien-2-yl | H | 5-$CH_3S(O)_2$-benzimidazol-1-yl | R isomer | — | 592 |
| 10 | $CH_3S(O)_2$ | 4-Chlorothien-2-yl | H | 5-$CH_3S(O)_2$-benzimidazol-1-yl | R isomer | — | 592 |
| 11 | $CH_3S(O)_2$ | 3,5-Difluorophenyl | H | 5-$CH_3S(O)_2$-benzimidazol-1-yl | R isomer | — | 588 |
| 12 | $CH_3S(O)_2$ | 3,5-Difluorophenyl | H | 3-$CH_3$-5-$(CH_3)_2$CH-[1,2,4]triazol-4-yl | R isomer | — | 517 |
| 13 | $CH_3S(O)_2$ | Phenyl | H | 3-$CH_3$-[1,2,4]-oxadiazol-5-yl | S isomer | — | 440 |
| 14 | $CH_3S(O)_2$ | 3,5-Difluorophenyl | H | 2-((4-Chloro-phenyl)$CH_2$)-2H-tetrazol-5-yl | R isomer | — | 586 |
| 15 | $CH_3S(O)_2$ | 3,5-Difluorophenyl | H | 2-((4-$CH_3S(O)_2$-phenyl)$CH_2$)-2H-tetrazol-5-yl | R isomer | — | 630 |
| 16 | $CH_3S(O)_2$ | 3,5-Difluorophenyl | H | 5-Benzyl-2-methyl-2H-pyrazol-3-yl | R isomer | hydrochloride | 564 |
| 17 | $CH_3S(O)_2$ | 3-Cl, 5-F-phenyl | H | 5-$CH_3S(O)_2$-benzimidazol-1-yl | R isomer | — | 604 |
| 18 | $CH_3S(O)_2$ | 3,5-Difluorophenyl | H | 2-ethyl-5-(4-fluorobenzyl)-2H-pyrazol-3-yl | R isomer | — | 596 |
| 19 | $CH_3S(O)_2$ | 3,5-Difluorophenyl | H | 4-amino-1,3-thiazol-2-yl | R isomer | — | 492 |
| 20 | $CH_3S(O)_2$ | 3,5-Difluorophenyl | H | 5-methylimidazolidine-2,4-one-3-yl | R isomer | — | 506 |
| 21 | $CH_3S(O)_2$ | 3,5-Difluorophenyl | H | 5-phenylimidazolidine-2,4-one-3-yl | R isomer | — | 568 |
| 22 | $CH_3S(O)_2$ | 3,5-Difluorophenyl | H | 2-(4-chlorobenzyl)-1,3-thiazol-5-yl | R isomer | — | 601 |
| 23 | $CH_3S(O)_2$ | 3,5-Difluorophenyl | H | 5-ethylimidazolidine-2,4-one-3-yl | R isomer | — | 520 |
| 24 | $CH_3S(O)_2$ | 3,5-Difluorophenyl | H | 2-methyl-2H-tetrazol-5-yl | R isomer | — | 476 |
| 25 | $CH_3S(O)_2$ | 3,5-Difluorophenyl | H | Indol-1-yl | R isomer | — | 509 |
| 26 | $CH_3S(O)_2$ | 3,5-Difluorophenyl | H | 4H-[1,2,4]triazol-4-yl | R isomer | — | 461 |
| 27 | $CH_3S(O)_2$ | 3,5-Difluorophenyl | H | 3,5-dimethyl-[1,2,4]triazol-4-yl | R isomer | — | 489 |
| 28 | $CH_3S(O)_2$ | 3,5-Difluorophenyl | H | 5-cyano-benzimidazol-1-yl | R isomer | — | 535 |
| 29 | $CH_3S(O)_2$ | 3,5-Difluorophenyl | H | Benzimidazol-1-yl | R isomer | — | 510 |
| 30 | $CH_3S(O)_2$ | 3,5-Difluorophenyl | H | 2-methyl-5-$CH_3S(O)_2$-benzimidazol-1-yl | R isomer | — | 602 |

TABLE II

Table II comprises compounds of formula (I) wherein A is $CH_2CH_2$.

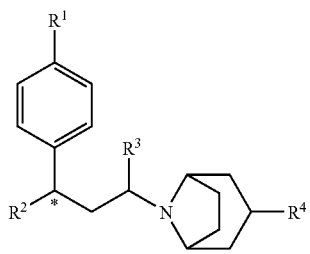

| Compound No. | $R^1$ | $R^2$ | $R^3$ | $R^4$ | *Chirality | LCMS (MH+) |
|---|---|---|---|---|---|---|
| 1 | $CH_3S(O)_2$ | 3,5-Difluorophenyl | H | 3-isopropyl-5-methyl-4H-1,2,4-triazol-4-yl (exo) | R isomer | 543 |
| 2 | $CH_3S(O)_2$ | 3,5-Difluorophenyl | H | 5-(methylsulfonyl)-1H-benzimidazole (endo) | R isomer | 614 |
| 3 | $CH_3S(O)_2$ | 3,5-Difluorophenyl | H | 5-(methylsulfonyl)-1H-benzimidazole (exo) | R isomer | 614 |

The compounds of the invention can be prepared as shown in the processes on pages marked Schemes 1 and 2 below. (In Schemes 1 and 2 Ac is acetyl; Bu is butyl; LDA is lithium diisopropylamide; TMEDA is N,N,N',N'-tetramethylethyenediamine; and, Tf is triflate.)

A compound of the invention can be prepared by reductive amination of a compound of formula (II) or (IIa):

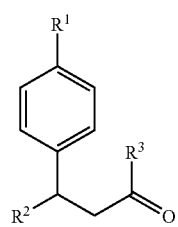
(II)

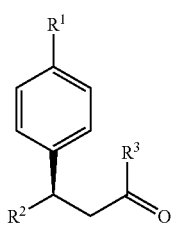
(IIa)

with a compound of formula (III):

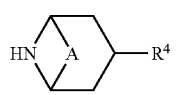
(III)

in the presence of $NaBH(OAc)_3$ (wherein Ac is $C(O)CH_3$) and acetic acid, in a suitable solvent (such as a $C_{1-6}$ aliphatic alcohol, for example ethanol) at room temperature (for example 10-30° C.).

Compounds of formula (III) can be prepared by removal of the protecting group (PG) from a compound of formula (I), for example where PG is benzyloxylcarbonyl or benzyl removal may be effected by hydrogenation (for example hydrogen in the presence of palladium on carbon catalyst); where PG is tert-butyloxycarbonyl removal may be effected by treatment with acid (such as hydrochloric acid or trifluoroacetic acid).

(IV)

Compounds of formula (IVa) can be made by first reducing a compound of formula (Va):

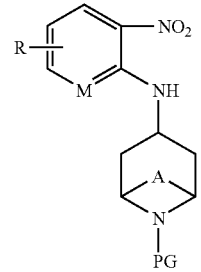
(Va)

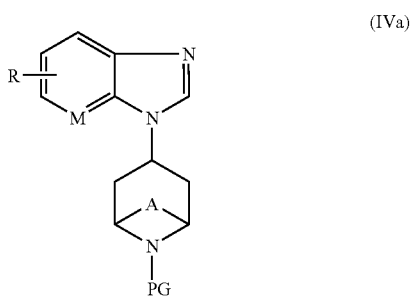
(IVa)

and then cyclising the product so formed. (For example cyclising in the presence of trimethylorthoformate and para-toluenesuphonic acid monohydrate.)

A compound of formula (Va) can be prepared by coupling a compound of formula (VIa):

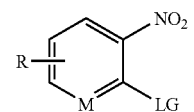
(VIa)

wherein LG is a leaving group (such as fluorine), with a compound of formula (VII):

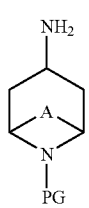
(VII)

in the presence of a base. Compounds of formula (VIa) can be made by nitration of the respective chloroheteroaryl or respective chloroheteroaryl N-oxide (followed by reduction to remove the N-oxide); or by chlorination of an oxo-nitro-heteroaryl (such as 3-nitropyridin-4-one).

Compounds of formula (IVb) can be prepared from a compound of formula (Vb) using a "one-pot", two-step procedure by first activating the amide with, for example, phosphorous oxychloride in the presence of a base (such as pyridine) and reacting with an acyl hydrazide, then by cyclising in the presence of an acid at elevated temperature (such as para-toluenesuphonic acid in refluxing toluene).

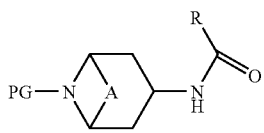 (Vb)

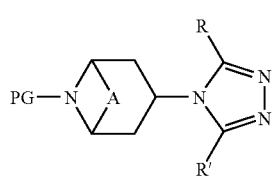 (IVb)

Compounds of formula (Vb) can be prepared from a compound of formula (VII) by reaction with an activated carboxylic acid or with a carbonyl chloride in the presence of a base.

Compounds of formula (IVc) can be prepared by first activating the acid of a compound of formula (Vc) and reacting with an N-hydroxy-amidine $RC(NOH)NH_2$, then by cyclisation under elevated temperature in a suitable solvent such as dioxan.

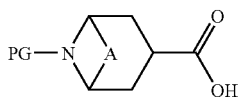 (Vc)

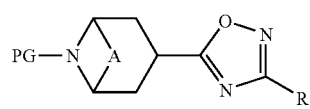 (IVc)

Compounds of formula (IVd) can be prepared by addition of azide to a compound of formula (Vd) then by alkylation of the product so formed.

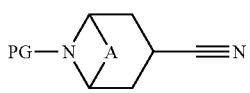 (Vd)

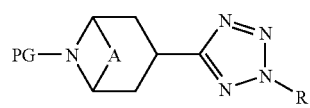 (IVd)

Compounds of formula (IVe) and (IVf) can be prepared by reaction of a compound of formula (Ve) with an alkyl hydrazine $R'NHNH_2$. Compounds of formula (Ve) can be made by condensation of a compound of formula (VIe) with an ester $RC(O)_2R''$.

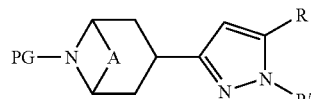 (IVe)

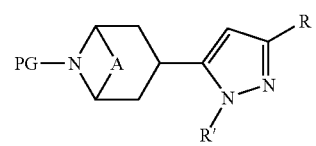 (IVf)

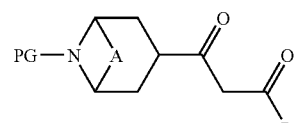 (Ve)

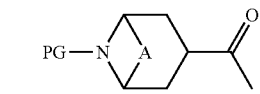 (VIe)

Compounds of formula (IVg) can be prepared by reaction of a compound of formula (Vg) with a 1,3-di-ketone $RC(O)CH_2C(O)R'$.

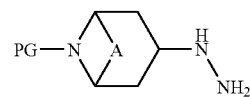 (Vg)

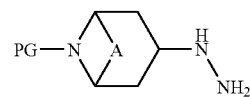 (IVg)

A compound of the invention can be prepared by alkylation of a compound of formula (VIII) or (VIIIa):

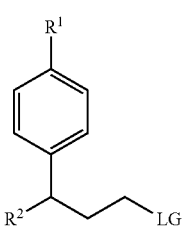 VIII

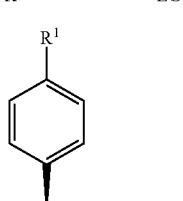 VIIIa with a compound of formula (III)

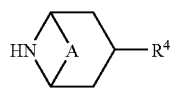

(III)

in the presence of a suitable base, such as potassium carbonate or triethylamine, in a suitable solvent, such as acetonitrile or THF at room temperature (for example 10-30° C.).

The starting materials for these preparative methods and Schemes are either commercially available or can be prepared by literature methods, adapting literature methods or by following or adapting Methods herein described.

In a further aspect the invention provides processes for preparing the compounds of the invention. Many of the intermediates in the processes are novel and these are provided as further features of the invention.

The compounds of the invention have activity as pharmaceuticals, in particular as modulators (such as agonists, partial agonists, inverse agonists or antagonists) of chemokine receptor (especially CCR5) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

The compounds of the present invention are also of value in inhibiting the entry of viruses (such as human immunodeficiency virus (HIV)) into target cells and, therefore, are of value in the prevention of infection by viruses (such as HIV), the treatment of infection by viruses (such as HIV) and the prevention and/or treatment of acquired immune deficiency syndrome (AIDS).

According to a further feature of the invention there is provided a compound of the invention, or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR5 receptor activity) in a warm blooded animal, such as man, in need of such treatment, which comprises administering to said animal an effective amount of a compound of the present invention, or a pharmaceutically acceptable salt thereof or a solvate thereof.

The present invention also provides the use of a compound of the invention, or a pharmaceutically acceptable salt thereof or a solvate thereof, as a medicament, especially a medicament for the treatment of transplant rejection, respiratory disease, psoriasis or rheumatoid arthritis (especially rheumatoid arthritis). [Respiratory disease is, for example, COPD, asthma {such as bronchial, allergic, intrinsic, extrinsic or dust asthma, particularly chronic or inveterate asthma (for example late asthma or airways hyper-responsiveness)} or rhinitis {acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}; and is particularly asthma or rhinitis].

In another aspect the present invention provides the use of a compound of the invention, or a pharmaceutically acceptable salt thereof or a solvate thereof, in the manufacture of a medicament for use in therapy (for example modulating chemokine receptor activity (especially CCR5 receptor activity (especially rheumatoid arthritis)) in a warm blooded animal, such as man).

The invention also provides a compound of the invention, or a pharmaceutically acceptable salt thereof or a solvate thereof, for use as a medicament, especially a medicament for the treatment of rheumatoid arthritis.

In another aspect the present invention provides the use of a compound of the invention, or a pharmaceutically acceptable salt thereof or a solvate thereof, in the manufacture of a medicament for use in therapy (for example modulating chemokine receptor activity (especially CCR5 receptor activity (especially rheumatoid arthritis)) in a warm blooded animal, such as man).

The invention further provides the use of a compound of the invention, or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle;

in a warm blooded animal, such as man.

The present invention further provides a method of treating a chemokine mediated disease state (especially a CCR5 mediated disease state) in a warm blooded animal, such as man, which comprises administering to a mammal in need of such treatment an effective amount of a compound of the invention, or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR5 receptor) activity, said ingredient is normally formulated in accordance with standard pharmaceutical practice as a pharmaceutical composition.

Therefore in another aspect the present invention provides a pharmaceutical composition which comprises a compound of the invention, or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of the invention, or a pharmaceutically acceptable salt thereof or a solvent thereof (hereafter Compound X), for therapeutic or prophylactic use in humans:

| (a) | |
|---|---|
| Tablet I | mg/tablet |
| Compound X | 100 |
| Lactose Ph. Eur. | 179 |
| Croscarmellose sodium | 12.0 |
| Polyvinylpyrrolidone | 6 |
| Magnesium stearate | 3.0 |

| (b) | |
|---|---|
| Tablet II | mg/tablet |
| Compound X | 50 |
| Lactose Ph. Eur. | 229 |
| Croscarmellose sodium | 12.0 |
| Polyvinylpyrrolidone | 6 |
| Magnesium stearate | 3.0 |

| (c) | |
|---|---|
| Tablet III | mg/tablet |
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

| (d) | |
|---|---|
| Capsule | mg/capsule |
| Compound X | 10 |
| Lactose Ph. Eur. | 389 |
| Croscarmellose sodium | 100 |
| Magnesium stearate | 1.0 |

| (e) | |
|---|---|
| Injection I | (50 mg/mL) |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)-(c) may be enteric coated by conventional means, for example to provide a coating of cellulose acetate phthalate.

The invention further relates to combination therapies or compositions wherein a compound of the invention, or a pharmaceutically acceptable salt, solvate or a solvate of a salt thereof, or a pharmaceutical composition comprising a compound of the invention, or a pharmaceutically acceptable salt, solvate or a solvate of a salt thereof, is administered concurrently (possibly in the same composition) or sequentially with an agent for the treatment of any one of the above disease states.

In particular, for the treatment of the inflammatory diseases rheumatoid arthritis, psoriasis, inflammatory bowel disease, COPD, asthma and allergic rhinitis a compound of the invention can be combined with a TNF-α inhibitor (such as an anti-TNF monoclonal antibody (such as Remicade, CDP-870 and D.sub2.E.sub7.), or a TNF receptor immunoglobulin molecule (such as Enbrel.reg.)), a non-selective COX-1/COX-2 inhibitor (such as piroxicam or diclofenac; a propionic acid such as naproxen, flubiprofen, fenoprofen, ketoprofen or ibuprofen; a fenamate such as mefenamic acid, indomethacin, sulindac or apazone; a pyrazolone such as phenylbutazone; or a salicylate such as aspirin), a COX-2 inhibitor (such as meloxicam, celecoxib, rofecoxib, valdecoxib or etoricoxib) low dose methotrexate, lefunomide; ciclesonide; hydroxychloroquine, d-penicillamine or auranofin, or parenteral or oral gold.

The present invention still further relates to the combination of a compound of the invention together with:

- a leukotriene biosynthesis inhibitor, a 5-lipoxygenase (5-LO) inhibitor or a 5-lipoxygenase activating protein (FLAP) antagonist, such as zileuton, ABT-761, fenleuton, tepoxalin, Abbott-79175, Abbott-85761, an N-(5-substituted)-thiophene-2-alkylsulfonamide, a 2,6-di-tert-butylphenol hydrazones, a methoxytetrahydropyran such as Zeneca ZD-2138, SB-210661, a pyridinyl-substituted 2-cyanonaphthalene compound such as L-739,010; a 2-cyanoquinoline compound such as L-746,530; an indole or quinoline compound such as MK-591, MK-886 or BAYx1005;
- a receptor antagonist for a leukotriene LTB.sub4., LTC.sub4., LTD.sub4. or LTE.sub4. selected from the group consisting of a phenothiazin-3-one such as L-651,392; an amidino compound such as CGS-25019c; a benzoxalamine such as ontazolast; a benzenecarboximidamide such as BIIL 284/260; or a compound such as zafirlukast, ablukast, montelukast, pranlukast, verlukast (MK-679), RG-12525, Ro-245913, iralukast (CGP 45715A) or BAYx7195;
- a PDE4 inhibitor including an inhibitor of the isoform PDE4D;
- an antihistaminic H.sub1. receptor antagonist such as cetirizine, loratadine, desloratadine, fexofenadine, astemizole, azelastine or chlorpheniramine;
- a gastroprotective H.sub2. receptor antagonist;
- an α.sub1.- and α.sub2.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride or ethylnorepinephrine hydrochloride; an anticholinergic agent such as ipratropium bromide, tiotropium bromide, oxitropium bromide, pirenzepine or telenzepine;
- a β.sub1.- to β.sub4.-adrenoceptor agonist such as metaproterenol, isoproterenol, isoprenaline, albuterol, salbutamol, formoterol, salmeterol, terbutaline, orciprenaline, bitolterol mesylate or pirbuterol, or a methylxanthanine including theophylline and aminophylline; sodium cromoglycate; or a muscarinic receptor (M1, M2, and M3) antagonist;
- an insulin-like growth factor type I (IGF-1) mimetic;
- an inhaled glucocorticoid with reduced systemic side effects, such as prednisone, prednisolone, flunisolide, triamcinolone acetonide, beclomethasone dipropionate, budesonide, fluticasone propionate or mometasone furoate;
- an inhibitor of a matrix metalloprotease (MMP), such as a stromelysin, a collagenase, or a gelatinase or aggrecanase; such as collagenase-1 (MMP-1), collagenase-2 (MMP-8), collagenase-3 (MMP-13), stromelysin-1 (MMP-3), stromelysin-2 (MMP-10), and stromelysin-3 (MMP-11) or MMP-12;
- a modulator of chemokine receptor function such as CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the $C-X_3-C$ family;
- an osteoporosis agent such as roloxifene, droloxifene, lasofoxifene or fosomax;
- an immunosuppressant agent such as FK-506, raparnycin, cyclosporine, azathioprine or methotrexate;
- a compound useful in the treatment of AIDS and/or HIV infection for example: an agent which prevents or inhibits the viral protein gp 120 from engaging host cell CD4 {such as soluble CD4 (recombinant); an anti-CD4 antibody (or modified/recombinant antibody) for example PRO542; an anti-group 120 antibody (or modified/recombinant antibody); or another agent which interferes with the binding of group 120 to CD4 for example BMS806}; an agent which prevents binding to a chemokine receptor, other than CCR5, used by the HIV virus {such as a CXCR4 agonist or antagonist or an anti-CXCR4 antibody}; a compound which interferes in the fusion between the HIV viral envelope and a cell membrane {such as an anti-group 41 antibody; enfuvirtide (T-20) or T-1249}; an inhibitor of DC-SIGN (also known as CD209) {such as an anti-DC-SIGN antibody or an inhibitor of DC-SIGN binding}; a nucleoside/nucleotide analogue reverse transcriptase inhibitor {for example zidovudine (AZT), nevirapine, didanosine (ddI), zalcitabine (ddC), stavudine (d4T), lamivudine (3TC), abacavir, adefovir or tenofovir (for example as free base or as disoproxil flumarate)}; a non-nucleoside reverse transcriptase inhibitor {for example nevirapine, delavirdine or efavirenz}; a protease inhibitor {for example ritonavir, indinavir, saquinavir (for example as free base or as mesylate salt), nelfinavir (for example as free base or as mesylate salt), amprenavir, lopinavir or atazanavir (for example as free base or as sulphate salt)}; a ribonucleotide reductase inhinbitor {for example hydroxyurea}; or an antiretroviral {for example emtricitabine}; or,
- an existing therapeutic agent for the treatment of osteoarthritis, for example a non-steroidal anti-inflammatory agent (hereinafter NSAID's) such as piroxicam or diclofenac, a propionic acid such as naproxen, flubiprofen, fenoprofen, ketoprofen or ibuprofen, a fenamate such as mefenamic acid, indomethacin, sulindac or apazone, a pyrazolone such as phenylbutazone, a salicylate such as aspirin, a COX-2 inhibitor such as celecoxib, valdecoxib, rofecoxib or etoricoxib, an analgesic or intra-articular therapy such as a corticosteroid or a hyaluronic acid such as hyalgan or synvisc, or a P2X7 receptor antagonist.

The present invention still further relates to the combination of a compound of the invention together with: (i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitor including a VLA-4 antagonist; (vi) a cathepsin; (vii) a MAP kinase inhibitor; (viii) a glucose-6 phosphate dehydrogenase inhibitor; (ix) a kinin-B.sub1.- and B.sub2.- receptor antagonist; (x) an anti-gout agent, e.g., colchicine; (xi) a xanthine oxidase inhibitor, e.g., allopurinol; (xii) an uricosuric agent, e.g., probenecid, sulfinpyrazone or benzbromarone; (xiii) a growth hormone secretagogue; (xiv) a transforming growth factor (TGFβ); (xv) a platelet-derived growth factor (PDGF); (xvi) a fibroblast growth factor, e.g., basic fibroblast growth factor (bPGF); (xvii) a granulocyte macrophage colony stimulating factor (GM-CSF); (xviii) a capsaicin cream; (xix) a Tachykinin NK.sub1. and NK.sub3.

receptor antagonist selected from the group consisting of NKP-608C; SB-233412 (talnetant); and D-4418; (xx) an elastase inhibitors selected from the group consisting of UT-77 and ZD-0892; (xxi) a TNFα converting enzyme inhibitor (TACE); (xxii) an induced nitric oxide synthase inhibitor (iNOS); or (xxiii) a chemoattractant receptor-homologous molecule expressed on TH2 cells (a CRTH2 antagonist).

The invention will now be illustrated by the following non-limiting Examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 mL disposable syringe and supported by a porous disc, obtained from Varian, Harbor City, Calif., USA under the name "Mega Bond Elut SI". Where an "Isolute™ SCX column" is referred to, this means a column containing benzenesulphonic acid (non-endcapped) obtained from International Sorbent Technology Ltd., 1st House, Duffryn Industial Estate, Ystrad Mynach, Hengoed, Mid Glamorgan, UK. Where "Argonaut™ PS-tris-amine scavenger resin" is referred to, this means a tris-(2-aminoethyl)amine polystyrene resin obtained from Argonaut Technologies Inc., 887 Industrial Road, Suite G, San Carlos, Calif., USA.

(iv) in general, the course of reactions was followed by TLC and reaction times are given for illustration only;

(v) yields, when given, are for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using per-deuterio DMSO ($CD_3SOCD_3$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (APCI) mode using a direct exposure probe; where indicated ionisation was effected by electrospray (ES); where values for m/z are given, generally only ions which indicate the parent mass are reported, and unless otherwise stated the mass ion quoted is the positive mass ion—$(M+H)^+$;

(x) LCMS characterisation was performed using a pair of Gilson 306 pumps with Gilson 233 XL sampler and Waters ZMD4000 mass spectrometer. The LC comprised water symmetry 4.6×50 column C18 with 5 micron particle size. The eluents were: A, water with 0.05% formic acid and B, acetonitrile with 0.05% formic acid. The eluent gradient went from 95% A to 95% B in 6 minutes. Where indicated ionisation was effected by electrospray (ES); where values for m/z are given, generally only ions which indicate the parent mass are reported, and unless otherwise stated the mass ion quoted is the positive mass ion—$(M+H)^+$;

(xi) the compounds of the Examples and Methods were named using the IUPAC name program from Advanced Chemistry Development Inc, version 6.00; and, (xii) the following abbreviations are used:
DMSO dimethyl sulfoxide;
DMF N-dimethylformamide;
DCM dichloromethane;
THF tetrahydrofuran;
DIPEA N,N-diisopropylethylamine;
DIBAL Di-iso-butyl aluminium hydride
NMP N-methylpyrrolidinone;
HATU O-(7-Azabenzotriazol-1-yl)-N,N,N',N'-tetramethyluronium hexafluorophosphate;
HBTU O-(7-Benzotriazol-1-yl)-N,N,N',N'-tetramethyluronium hexafluorophosphate;
Boc tert-butoxycarbonyl
MeOH methanol;
EtOH ethanol; and
EtOAc ethyl acetate.

EXAMPLE 1

This Example illustrates the preparation of (R)-1-{1-[3-(3-fluoro-phenyl)-3-(4-methanesulfonyl-phenyl)-propyl]-piperidin-4-yl}-5-methanesulfonyl-1H-benzoimidazole (Compound No. 1 of Table I).

Under an argon atmosphere (R)-3-(3-fluoro-phenyl)-3-(4-methanesulfonylphenyl)-propionaldehyde (0.162 g) (Method O) and 5-methanesulfonyl-1-piperidin-4-yl-1H-benzoimidazole (0.112 g) (Method A) were dissolved in dichloromethane. A drop of acetic acid was added followed by sodium trisacetoxyborohydride (0.254 g) and the reaction mixture was stirred at ambient temperature for 18 hours, then partitioned between dichloromethane (2×50 mL) and 2M aqueous sodium hydroxide solution (50 mL). The organic liquors were washed with saturated brine, dried (MgSO4) and evaporated to dryness on the rotary evaporator. The residue was purified on a 20 g silica cartridge eluting with a 0 to 30% methanol in ethyl acetate gradient over 30 minutes at 20 mL per minute to yield the title compound as a solid (0.056 g). NMR ($CDCl_3$): 2.17 (m, 6H), 2.33 (m, 4H), 3.04 (s, 3H), 3.08 (m, 4H), 4.18 (t, 1H), 4.25 (m, 1H), 6.92 (m, 2H), 7.04 (d, 1H), 7.39 (m, 1H), 7.45 (d, 2H), 7.57 (d, 1H), 7.89 (d, 2H), 8.19 (s, 1H), 8.42 (s, 1H).

The procedure described in Example 1 can be repeated using different piperidines or piperidine hydrochlorides (such as 2-methyl-5-(methylsulfonyl)-1-piperidin-4-yl-1H-benzimidazole (Method A), 1-piperidin-4-yl-1H-benzimidazole-5-carbonitrile (Method A), 4-(3-isopropyl-5-methyl-[1,2,4]triazol-4-yl)-piperidine (Method B), 4-[3-(4-methanesulfonyl-benzyl)-[1,2,4]oxadiazol-5-yl]-piperidine hydrochloride (Method C), 4-(3-benzyl-[1,2,4]oxadiazol-5-yl)-piperidine hydrochloride (Method D), 4-[3-(4-methylsulfanyl-benzyl)-[1,2,4]oxadiazol-5-yl]-piperidine hydrochloride (Method E), 4-(3-methyl-[1,2,4]oxadiazol-5-yl)-piperidine (Method F), 4-[2-(4-chloro-benzyl)-2H-tetrazol-5-yl]-piperidine (Method G), 4-[2-(4-methanesulfonyl-benzyl)-2H-tetrazol-5-yl]-piperidine (Method H), or 4-(5-benzyl-2-methyl-2H-pyrazol-3-yl)-piperidine (Method I), 4-[2-ethyl-5-(4-fluoro-benzyl)-2H-pyrazol-3-yl]-piperidine (Method J), 4-[2-(4-chlorobenzyl)-1,3-thiazol-4-yl]piperidine (Method R), 4-(2-Methyl-2H-tetrazol-5-yl)-piperidine (Method S), 2-piperidine-4-yl-1,3-thiazol-4-amine, 5-ethyl-3-piperidin-4-ylimidazolidine-2,4-dione (Method T), 5-phenyl-3-piperidin-4-ylimidazolidine-2,4-dione (Method T), 5-methyl-3-piperidin-4-ylimidazolidine-2,4-dione (Method T), 4-(4H-1,2,4-triazol-4-yl)piperidine Method U), 4-(3,5-dimethyl-4H-1,2,4-triazol-4-yl)piperidine (Method V), 3-(3-isopropyl-5-methyl-4H-1,2,4-triazol-4-yl)-exo-8-azabicyclo [3.2.1]octane (Method W), 1-endo-(8-azabicyclo[3.2.1]oct-3-yl)-5-(methylsufonyl) 1H-benzamidazole (Method X), 1-exo-(8-azabicyclo[3.2.1]oct-3-yl)-5-(methylsufonyl)-1H-benzamidazole (Method Y), in place of 5-methanesulfonyl-1-piperidin-4-yl-1H-benzoimidazole and different aldehydes (such as (R)-3-(4-methanesulfonyl-phenyl)-3-thiophen-2-yl-propionaldehyde (Method J), (R)-3-(4-methanesulfonyl-phenyl)-3-thiophen-3-yl-propionaldehyde (Method K), (R)-3-(4-methanesulfonyl-phenyl)-3-(5-chlorothiophen-2-yl)-propionaldehyde (Method L), (R)-3-(4-methanesulfonyl-phenyl)-3-(4-chlorothiophen-2-yl)-propionaldehyde (Method M), (S)-3-phenyl-3-(4-methanesulfonylphenyl)propionaldehyde (Method N), or (R)-3-(3,5-difluorophenyl)-3-(4-methanesulfonylphenyl) propionaldehyde (Method P), or (R)-3-(3-chloro-5-fluorophenyl)-3-(4-methanesulfonylphenyl)propionaldehyde (Method Q), in place of (R)-3-(3-fluoro-phenyl)-3-(4-methanesulfonylphenyl)-propionaldehyde.

EXAMPLE 2

This Example illustrates the preparation of 1-(1-{(3R)-3-(3,5-difluorophenyl)-3-[4-(methylsulfonyl)phenyl)phenyl] propyl}piperidin-4-yl)-1H-indole (Compound No. 25 of Table I).

Step 1: Tosyl chloride (3 g) was added portionwise to pyridine (50 ml) at 5° C., followed by a solution of (3R)-3-(3,5-difluorophenyl)-3-[4-(methylsulfonyl)phenyl]propan-1-ol (3.1 g) in pyridine (15 ml) and the resulting mixture was stirred at room temperature for 18 hours. The reaction mixture was poured onto ice/2N HCl and extracted with diethyl ether (×2). The organic extracts were dried and evaporated to dryness to give (3R)-3-(3,5-difluorophenyl)-3-[4-(methylsulfonyl)phenyl]propyl 4-methylbenzenesulfonate as a solid. Yield 2.9 g. NMR (CDCl$_3$): 2.4 (m, 2H), 2.5 (s, 3H), 3.05 (s, 3H), 3.95 (m, 2H), 4.2 (t, 1H), 6.7 9 m, 3H), 7.3 9 m, 4H), 7.75 (d, 2H), 7.85 (d, 2H).

Step 2: A mixture of 1-piperidin-4-yl-1H-indole hydrochloride (450 mg), (3R)-3-(3,5-difluorophenyl)-3-[4-(methylsulfonyl)phenyl]propyl 4-methylbenzenesulfonate (760 mg) and potassium carbonate (500 mg) in acetonitrile (30 ml) was refluxed for 18 hours. The reaction mixture was concentrated and partitioned between ethyl acetate and water. The organic extracts were dried and evaporated to dryness. The residue was purified by chromatography on silica eluting with ethyl acetate to give the title compound as a solid. Yield 200 mg. NMR (CDCl$_3$): 2.0-2.4 (m, 10H), 3.0-3.05 (m, 2H), 3.05 (s, 3H), 4.2 (m, 2H), 6.55 (d, 1H), 6.7 (m, 3H), 7.1-7.3 (m, 3H), 7.4 (d, 1H), 7.5 (d, 2H), 7.65 (d, 1H), 7.9 (d, 2H).

Additional NMR Data:

Compound No. 2 of Table I: NMR (CDCl$_3$): 1.70-2.34 (m, 11H), 2.53 (s, 3H), 3.00 (m, 5H), 3.18 (m, 1H), 4.12 (m, 1H), 6.92 (m, 2H), 7.02 (d, 1H), 7.26 (m, 1H), 7.43 (d, 2H), 7.87 (d, 2H).

Compound No. 3 of Table I: NMR: 2.08 (2H, m), 2.22 (2H, m), 2.61(2H, m), 2.92 (2H, m), 3.01 (2H, m), 3.18 (3H, s), 3.21 (2H, s), 3.29 (1H, m), 3.59 (2H, m), 4.20 (1H, t), 4.24 (2H, m).

Compound No. 4 of Table I: NMR: 2.08 (2H, m), 2.21 (2H, m), 2.62 (2H, m), 2.91 (2H, m), 3.01 (2H, m), 3.17 (3H, s), 3.27 (1H, m), 3.58 (2H, m), 4.08 (2H, s), 4.20 (1H, m), 7.32 (10H, m), 7.64 (2H, m), 7.87 (2H, m), 10.90 (1H, br s).

Compound No. 5 of Table I: NMR (CDCl$_3$): 2.19 (m, 8H), 2.36 (m, 4H), 3.03 (s, 3H), 3.06 (m, 1H), 3.10 (s, 3H), 4.18 (m, 1H), 4.25 (m, 1H), 7.24 (m, 5H), 7.47 (d, 2H), 7.60 (d, 1H), 7.84 (d, 2H), 8.19 (s, 1H), 8.40 (s, 1H).

Compound No. 6 of Table I: NMR: 2.07 (2H, m), 2.22 (2H, m), 2.45 (3H, s), 2.60 (2H, m), 2.92 (2H, m), 3.02 (2H, m), 3.59 (2H, m), 3.59 (2H, dd), 4.04 (2H, s), 4.20 (1H, t), 7.24 (2H, m), 7.33 (2H, m) 7.40 (2H, m), 7.87 (2H, m), 10.71 (1H, br s).

Compound No. 7 of Table I: NMR (CDCl$_3$): 2.10 (m, 2H), 2.20 (m, 6H), 2.35 (m, 2H), 2.89 and 4.35 (m, 1H), 3.05 (s, 3H), 3.12 (m, 5H), 4.25 (m, 2H), 6.90 (d, 1H), 7.08 (s, 1H), 7.30 (s, 1H), 7.45 (d, 1H), 7.60 (m, 1H), 7.85 (d, 2H), 8.18 (s, 1H), 8.39 (s, 1H).

Compound No. 8 of Table I: NMR (CDCl$_3$): 2.22 (m, 9H), 2.40 (m, 2H), 3.05 (s, 3H), 3.13 (s, 3H), 4.28 (m, 1H), 4.40 (m, 1H), 6.93 (m, 2H), 7.20 (d, 1H), 7.50 (m, 2H), 7.60 (d, 1H), 7.88 (m, 3H), 8.20 (s, 1H), 8.41 (s, 1H).

Compound No. 9 of Table I: NMR (CDCl$_3$): 2.20 (m, 9H), 2.39 (m, 2H), 3.08 (s, 3H), 3.13 (s, 3H), 4.25 (m, 1H), 4.31 (m, 1H), 6.64 (d, 1H), 6.77 (d, 1H), 7.46 (d, 2H), 7.60 (d, 1H), 7.88 (m, 3H), 8.20 (s, 1H), 8.41 (s, 1H).

Compound No. 10 of Table I: NMR (CDCl$_3$) 2.20 (m, 9H), 2.39 (m, 2H), 3.07 (s, 3H), 3.10 (s, 3H), 4.26 (m, 1H), 4.38 (m, 1H), 6.77 (s, 1H), 7.00 (s, 1H), 7.49 (d, 2H), 7.60 (d, 1H), 7.89 (m, 3H), 8.20 (s, 1H), 8.40 (s, 1H).

Compound No. 11 of Table I: NMR (CDCl$_3$): 2.20 (m, 10H), 2.38 (m, 2H), 3.04 (s, 3H), 3.10 (s, 3H), 4.19 (m, 1H), 4.23 (m, 1H), 6.75 (m, 1H), 6.80 (m, 2H), 7.41 (d, 2H), 7.60 (d, 1H), 7.88 (m, 3H), 8.19 (s, 1H), 8.41 (s, 1H).

Compound No. 12 of Table I: NMR (CDCl$_3$): 1.40 (d, 6H), 1.82 (m, 2H), 2.10 (m, 5H), 2.30 (m, 4H), 2.55 (s, 3H), 3.03 (m, 2H), 3.08 (s, 3H), 3.90 (m, 1H), 4.15 (m, 1H), 6.64 (m, 1H), 6.80 (m, 2H), 7.44 (d, 2H), 7.90 (d, 2H).

Compound No. 13 of Table I: NMR: 2.32(3H, m), 2.60-2.92 (9H, m), 2.95 (3H, s), 3.40 (2H, m), 3.64 (2H, m), 4.06 (1H, m), 7.18 (2H, m), 7.26 (2H, m), 7.42 (2H, m), 7.80 (2H, m).

Compound No. 14 of Table I: NMR (CDCl$_3$): 1.9 (m, 2H), 2.05 (m, 4H), 2.25 (m, 4H), 2.9 (m, 3H), 3.05 (s, 3H), 4.2 (m, 1H), 5.7 (s, 2H), 6.7 (m, 1H), 6.75 (d, 2H), 7.3 (m, 4H), 7.4 (d, 2H), 7.9 (d, 2H).

Compound No. 15 of Table I: NMR (CDCl$_3$): 1.9 (m, 2H), 2.1 (m, 4H), 2.25 (m, 4H), 2.9 (m, 3H), 3.05 (s, 6H), 4.2 (m, 1H), 5.8 (s, 2H), 6.65 (m, 1H), 6.75 (d, 2H), 7.45 (d, 2H), 7.55 (d, 2H), 7.9 (d, 2H), 8.0 (d, 2H).

Compound No. 16 of Table I: NMR (CDCl$_3$): 1.65 (m, 2H), 1.83 (d, 2H), 1.99 (t, 2H), 2.23 (m, 4H), 2.48 (tt, 2H), 2.89 (t, 2H), 3.03 (s, 3H), 3.75 (s, 3H), 3.92 (s, 2H), 4.15 (m, 1H), 5.76 (s, 1H), 6.66 (tt, 1H), 6.75 (m, 2H), 7.19 (m, 1H), 7.26 (m, 4H), 7.41 (d, 2H), 7.87 (d, 2H).

Compound No. 17 of Table I: NMR (CDCl$_3$): 2.2 (m, 9H), 2.35 (m, 2H), 3.05 (s, 3H), 3.1 (s, 3H), 3.1 (m, 1H), 4.2 (m, 1H), 4.25 (m, 1H), 6.85 (dd, 1H), 7.0 (dd, 1H), 7.05 (s, 1H), 7.45 (d, 2H), 7.55 (d, 1H), 7.9 (m, 3H), 8.2 (s, 1H), 8.45 (s, 1H).

Compound No. 18 of Table I: NMR (CDCl$_3$): 1.12-1.15 (t, 3H), 1.54-1.76 (m, 6H), 1.90-1.95 (t, 2H), 2.10-2.21 (m, 2H), 2.38-2.45 (tt, 1H), 2.80-2.86 (t, 2H), 2.97 (s, 3H), 3.83 (s, 3H), 3.94-3.99 (q, 2H), 4.06-4.10 (t, 1H), 5.65 (s, 1H), 6.56-6.62 (tt, 1H), 6.66-6.71 (m, 2H), 6.86-6.91 (m, 2H), 7.11-7.16 (m, 2H), 7.34-7.36 (d, 2H), 7.80-7.82 (d, 2H).

Compound No. 19 of Table I: NMR (CDCl₃):1.6 (m, 2H), 1.9-2.0 (m, 4H,) 2.1-2.2 (m, 4H), 2.4 (m, 1H), 2.8 (m, 2H), 3.0 (s, 3H), 4.1 (m, 1H), 4.7 (bs, 2H), 6.0 (s, 1H), 6.6(m, 1H), 7.0 (m, 2H), 7.4 (d, 2H), 7.8 (d, 2H).

Compound No. 20 of Table I: 1 NMR (CDCl₃): 1.4 (d, 3H), 1.6 (m, 2H), 2.0 (m, 2H), 2.1 (m, 4H), 2.4-2.5 (m, 2H), 2.9 (m, 2H), 3.0 (s, 3H), 3.9 (m, 11, 4.0 (q, 1H), 4.2 (m, 1H), 5.5 (s, 1H), 6.6 (m, 1H), 6.8 (m, 2H), 7.4 (d, 2H), 7.8 (d, 2H).

Compound No. 21 of Table I: NMR (CDCl₃): 1.6 (m, 2H), 2.0 (m, 2H), 2.2 (m, 4H), 2.4-2.5(m, 2H), 2.9 (m, 2H), 3.0 (m, 3H), 3.9 (m, 1H), 4.2 (m, 1H), 5.0 (s, 1H), 5.8 (s, 1H), 6.6 (m, 1H), 6.8 (m, 2H), 7.3-7.4 (m, 7H), 7.8 (d, 2H).

Compound No. 22 of Table I: NMR (CDCl₃): 1.75 (m, 2H), 2.05 (m, 4H), 2.3 (m, 4H), 2.75 (m, 1H), 2.95 (m, 2H), 3.05 (s, 3H), 4.15 (m, 1H), 4.25 (s, 2H), 6.65 (m, 1H), 6.8 (m, 3H), 7.3 (m, 4H), 7.45 (d, 2H), 7.9 (d, 2H).

Compound No. 23 of Table I: NMR (CDCl₃): 1.0 (t, 3H), 1.6 (m, 2H), 1.7-1.9 (m, 2H), 2.0 (m, 2H), 2.1 (m, 4H), 2.4-2.5 (m, 2H), 2.9 (m, 2H), 3.0 (m, 3H), 3.8 (m, 1H), 3.9 (m, 1H), 4.2 (m, 1H), 5.5 (s, 1H), 6.6 (m, 1H), 6.8 (m, 2H), 7.4(d, 2H), 7.8 (d, 2H).

Compound No. 24 of Table I: NMR (CDCl₃): 1.94-2.17 (6H, m), 2.25-2.42 (5H, m), 2.97 (3H, m), 3.02 (3H, s), 4.27 (3H, s), 6.58 (1H, t), 6.75 (2H, d), 7.43 (2H, d), 7.88 (2H, d).

Compound No. 25 of Table I: NMR (CDCl₃): 2.0-2.4 (m, 10H), 3.0-3.05 (m, 2H), 3.05 (s, 3H), 4.2 (m, 2H), 6.55 (d, 1H), 6.7 (m, 3H), 7.1-7.3 (m, 3H), 7.4 (d, 1H), 7.5 (d, 2H), 7.65 (d, 1H), 7.9 (d, 2H).

Compound No. 26 of Table I: NMR (CDCl₃): 1.9 (m, 2H), 2.0 (m, 4H), 2.25 (m, 4H), 2.9 (m, 2H), 3.2 (s, 3H), 4.1 (m, 1H), 4.25 (t, 1H), 7.05 (m, 1H), 7.2 (m, 2H), 7.65 (d, 2H), 7.85 (d, 2H), 8.6 (s, 2H).

Compound No. 27 of Table I: NMR (CDCl₃): 1.75 (m, 2H), 2.0 (m, 2H), 2.25 (m, 4H), 2.35 (s, 6H), 2.9 (m, 2H), 3.2 (s, 3H), 3.3 (m, 2H), 3.9 (m, 1H), 4.25 (m, 1H), 7.05 (m, 1H), 7.2 (m, 2H), 7.65 (d, 2H), 7.9 (d, 2H).

Compound No. 28 of Table I: NMR (CDCl₃): 1.5 (m, 4H), 2.05-2.3 (m, 6H), 3.0 (m, 5H), 4.1 (m, 2H), 6.6 (m, 1H), 6.7 (m, 2H), 7.4 (m, 2H), 7.5 (dd, 2H), 7.85 (d, 2H), 8.1 (m, 2H).

Compound No. 29 of Table I: NMR (CDCl₃): 1.5 (m, 2H), 2.05-2.3 (m, 8H), 2.95-3.0 (m, 2H), 3.0 (s, 3H), 4.15 (m, 2H), 6.6 (m, 1H), 6.75 (m, 2H), 7.2 (m, 2H), 7.35 (m, 3H), 7.75 (m, 1H), 7.85 (m, 2H), 7.95 (s, 1H).

Compound No. 30 of Table I: NMR (CDCl₃): 1.55 (m, 2H), 1.8 (m, 2H), 2.1 (m, 2H), 2.2 (m, 2H), 2.3 (m, 2H), 2.45 (m, 2H), 2.6 (s, 3H), 3.0 (s, 3H), 3.05 (s, 3H), 4.1 (m, 2H), 6.6 (m, 1H), 6.75 (m, 2H), 7.4 (d, 2H), 7.6 (d, 1H), 7.75 (d, 1H), 7.85 (d, 2H), 8.2 (d, 1H).

Compound No. 1 of Table II: NMR (CDCl₃): 1.31 (d, 6H), 1.58 (m, 4H), 1.94 (m, 2H), 2.13 (m, 4H), 2.25 (m, 2H), 2.466 (s, 3H), 2.92 (m, 1H), 2.966 (s, 3H), 3.24 (m, 2H), 4.2 (m, 2H), 6.61 (m, 1H), 6.7 (m, 2H), 7.366 (m, 2H), 7.825 (m, 2H).

Compound No. 2 of Table II: NMR (CDCl₃): 1.6 (m, 2H) 1.9 (m, 2H) 2.1-2.2 (m, 2H) 2.3 (m, 4H) 2.8 (m, 2H) 3.1 (s, 3H) 3.2 (s, 3H) 3.4 (m, 2H) 4.3 (m, 1H) 4.8 (m, 1H) 6.8 (m, 1H) 6.9 (m, 2H) 7.5 (d, 2H) 7,6 (d, 2H) 8.0 (m, 3H) 8.2 (s, 1H) 8.5 (s, 1H).

Compound No. 3 of Table II: NMR (CDCl₃): 1.8 (m, 2H) 2.0 (m, 4H) 2.2-2.3 (m, 4H) 2.4 (m, 2H) 3.0 (s, 3H) 3.1 (s, 3H) 3.4 (m, 2H) 4.3 (t, 1H) 4.6 (m, 1H) 6.7 (n, 1H) 6.8 (m, 1H) 7.4 (d, 2H) 7.6 (d, 2H) 7.9 (m, 3H) 8.2 (s, 1H) 8.4 (s, 1H)

Method A

5-Methanesulfonyl-1-piperidin-4-yl-1H-benzoimidazole

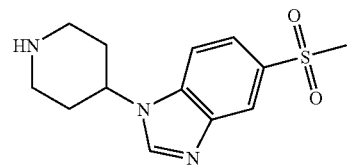

Step 1: 4-Amino-1-benzylpiperidine (87 g) was added slowly during 20 minutes to a stirred mixture of 2-fluoro-5-methylsulphonyl-nitrobenzene (100 g) and anhydrous sodium carbonate (35 g) in 500 mL DMSO, the internal temperature rose from 20° C. to 50° C. The mixture was stirred at 90° C. for 12 hours, then poured into ice/water and the yellow solid was filtered off, redissolved in dichloromethane, dried and evaporated to give 175 g N-(1-benzylpiperidin-4-yl)-2-nitro-4-methylsulphonylaniline.

Step 2: The crude material from step 1 (170 g) was dissolved in 3 litres of methanol in a pressure vessel, 20 g of moist 5% Pd/C catalyst was added and stirred under an atmosphere of hydrogen at 3 bar and 50° C. for one hour. The reaction was cooled, filtered and evaporated to give 133 g N-(1-benzylpiperidin-4-yl)-2-amino-4-methylsulphonylaniline as a brown solid.

Step 3: The crude material from step 2 (130 g) was stirred in 300 mL trimethylorthoformate containing 4-toluenesulphonic acid (8 g) at 90° C. for one hour, and collecting the methanol distillate. The reaction was cooled and filtered to give 108 g 1-(1-benzylpiperidin-4-yl)-5-methylsulphonyl-1H-benzimidazole as a brown solid.

Step 4: The crude material from step 3 (10 g) was dissolved in 1 litre of methanol in a pressure vessel, 20 g of moist 10% Pd/C catalyst and 100 mL acetic acid were added and stirred under an atmosphere of hydrogen at 5 bar and 50° C. for 8 hours. The reaction was cooled, filtered and evaporated. The residue was dissolved in water and basified with sodium hydroxide solution, extracted into dichloromethane, dried and evaporated. The brown solid was triturated with isopropanol, filtered, and washed with ether to give the title compound (60 g) as a pale grey solid; NMR: 2.00(m, 4H), 2.75(m, 2H), 3.15(m, 2H), 3.20(s, 3H), 4.60(m, 1H), 7.78 (dd, 1H), 7.85(d, 1H), 8.20(d, 1H), 8.56(s, 1H).

Preparation of 1-piperidin-4-yl-1H-benzimidazole-5-carbonitrile

In a similar manner to Method A step 1-3 was prepared tert-butyl-4-(5-cyano-1H-benzimidazol-1-yl)piperidin-1-carboxylate, except 4-fluoro-3-nitrobenzonitrile and tert-butyl 4-aminopiperidine-1-carboxylate was used. The tert-butyloxycarbonyl group was removed using the following method.

tert-Butyl-4-(5-cyano-1H-benzimidazol-1-yl)piperidin-1-carboxylate (326 mg) was dissolved in DCM (10 ml) and silica gel (10 g) was added and the mixture evaporated to dryness. Toluene (100 ml) was added and the mixture refluxed for 15 hours. The mixture was evaporated to dryness and the silica was then washed with dichloromethane. The organics were evaporated to a gum which was purified by chromatography on silica eluting with NH₃/MeOH/dichloromethane (2:18:80) to give the title compound as a solid. Yield 77 mg. NMR (d6 DMSO): 2.0 (m, 4H), 2.75 (m, 2H), 3.15 (m, 2H), 4.6 (m, 1H), 7.7 (d, 1H), 7.9 (d, 1H), 8.2 (s, 1H), 8.6 (s, 1H). MS 227 (MH⁺).

Preparation of 2-methyl-5-(methylsulfonyl)-1-piperidin-4-yl-1H-benzimidazole

In a similar manner to Method A steps 1-4, except using trimethylorthoacetate, was prepared 2-methyl-5-(methylsulfonyl)-1-piperidin-4-yl-1H-benzimidazole. MS 293 (MH⁺)

Method B

4(3-Isopropyl-5-methyl-[1,2,4]triazol-4-yl)-piperidine

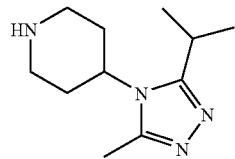

Step 1: To a solution of the 2-methyl-N-[1-(phenylmethyl)-4-piperidinyl]-propanamide (5.89 g) in pyridine (11.2 mL) and chloroform (15 mL) at 0° C. under Ar was added phosphorus oxychloride (6.33 mL). The mixture was allowed to warm to ambient temperature and stirred for 24 hours then evaporated. The residue was dissolved in chloroform (30 mL) and acetic hydrazide (3.36 g) added and the mixture heated at reflux for 5 hrs, diluted with saturated sodium hydrogen carbonate and extracted with dichloromethane, dried (MgSO₄) and evepourated. The residue was dissolved in 6M HCl (30 mL) and heated at reflux for 21 hours and then evaporated. Saturated potassium carbonate (300 mL) was added and extracted with dichloromethane, the organic layer was washed with brine, dried (MgSO₄) and evaporated. The resulting yellow oil was purified on silica (90 g) using 2% of a 7M ammonia soln in methanol in 98% dichloromethane to give a yellow solid (3.04 g); NMR (CDCl₃): 1.40 (d, 6H), 1.80 (m, 2H), 2.0-2.3 (m, 5H), 2.55 (s, 3H), 3.0-3.1 (m, 3H), 3.55 (s, 2H), 3.85 (m, 1H), 7.25-7.35 (m, 5H).

Step 2: The N-benzylpiperidine triazole (3.03 g) was dissolved in ethanol (50 mL) and 20% palladium hydroxide (0.70 g) and ammonium formate (3.22 g) added and the mixture heated at reflux for 150 minutes. The suspension was filtered through celite and the filtrate evaporated to give the product as a yellow solid (2.20 g). NMR (CDCl₃): 1.2 (d, 6H), 1.7 (m, 2H), 1.9 (m, 2H), 2.1 (br s, 1H), 2.4 (s, 3H), 2.6 (t, 2H), 3.0 (m, 2H), 3.1 (m, 1H), 4.0 (m, 1H).

Method C

4-[3-(4-Methanesulfonyl-benzyl)-[1,2,4]oxadiazol-5-yl]-piperidine hydrochloride

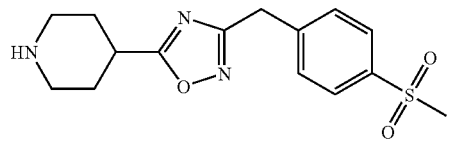

Step 1: tert-Butyl 4-{3-[4(methylthio)benzyl]-1,2,4-oxadiazol-5-yl}piperidine-1-carboxylate (3.10 g, 7.96 mmol) (Method E, step 1) was dissolved in dichloromethane(100 mL), at room temperature, under argon. 3-Chloroperbenzoic acid (60% wt, 6.87 g, 23.88 mmol) was added portionwise and stirred for 1 hour. Sodium metabisulfite (1M, 250 mL) was added and stirred and the organics separated and washed with 1N sodium hydroxide and brine, dried (MgSO₄) and solvents evaporated to a clear oil which crystallised upon addition of diethyl ether (50 mL). The solid was filtered, washed with a minimum of diethyl ether and dried to give tert-butyl 4-{3-[4-(methylsulfonyl)benzyl]-1,2,4-oxadiazol-5-yl}piperidine-1-carboxylate as a white fluffy solid (2.61 g, 78% yield); NMR (CDCl₃): 1.46 (9H, s), 1.61 (3H, s), 1.79 (2H, m), 2.04 (2H, m), 2.93 (2H, m), 3.04 (3H, s), 4.15 (2H, s), 7.53 (2H, d), 7.90 (2H, d).

Step 2: A premixed solution of acetyl chloride (0.97 mL, 11.86 mmol) was added dropwise to methanol (10 mL), stirred for 10 minutes and tert-butyl 4-{3-[4-(methylsulfonyl)benzyl]-1,2,4-oxadiazol-5-yl}piperidine-1-carboxylate (2.50 g, 5.93 mmol) was added and the mixture heated to reflux for 2 hours. The solvents were evaporated and the residue triturated with diethyl ether, filtered and dried to give the title compound as a fine white powder (2.05 g, 97%); NMR 1.97 (2H, m), 2.17(2H, dd), 3.02(2H, m), 3.31 (2H, m), 3.41 (1H, m), 4.25 (2H, s), 7.59 (2H, d), 7.89 (2H, d), 9.27(1H, br s), 9.35 (1H, br s); MS: 322 (MH+).

Method D 4-(3-Benzyl-[1,2,4]oxadiazol-5-yl)-piperidine hydrochloride

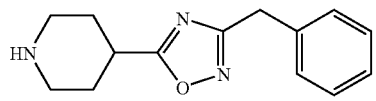

This was prepared from N'-hydroxy-2-phenylethanimidamide and 1-(tert-butoxycarbonyl)piperidine-4-carboxylic acid using a similar method to that used to prepare 4-{3-[4-(methylthio)benzyl]-1,2,4-oxadiazol-5-yl}piperidine hydrochloride (Method E, Steps 1, 2); NMR: 1.96 (2H, m), 2.15(2H, dd), 3.01(2H, t), 3.24 (2H, dd), 3.40 (1H, m), 4.09 (2H, s), 7.25 (5H, m), 9.31(2H, br s); MS: 244 (MH+).

Method E

4-{3-[4-(methylthio)benzyl]-1,2,4-oxadiazol-5-yl}piperidine hydrochloride

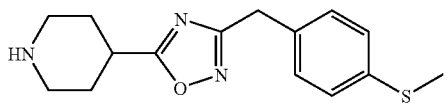

1-(tert-Butoxycarbonyl)piperidine-4-carboxylic acid (1.00 g, 4.36 mmol), 1-hydroxybenzotriazole (589 mg, 4.36 mmol) and N-methylmorpholine (0.97 mL, 8.72 mmol) were dissolved in diclomethane (50 mL), under argon, and (3-dimethylaminopropyl)carbodiimide hydrochloride (921 mg, 8.72 mmol) and N'-hydroxy-2-[4-(methylthio)phenyl]ethanimidamide (855 mg, 4.36 mmol) were added. The mixture was stirred at room temperature for 92 hours. The organics were washed with sodium hydroxide (0.1N) and citric acid (0.5M), dried (phase separating filter) and the solvent evaporated to give a yellow oil which was redissolved in 1,4-dioxane (100 mL) and heated to reflux for 5 hours, cooled and the solvent evaporated and chromatographed (50 g Silica Isolute, eluent 20% ethyl acetate/isohexane) to give a yellow oil, tert-butyl 4-{3-[4-(methylthio)benzyl]-1,2,4-oxadiazol-5-yl}piperidine-1-carboxylate (920 mg, 54%); NMR (CDCl$_3$): 1.46 (9H, s), 1.71-1.87 (2H, m), 2.03 (2H, m), 2.48 (3H, m), 2.92 (2H, t), 3.05 (1H, m), 4.00 (2H, s), 4.07 (2H, m), 7.24 (4H, m).

Step 2. Acetyl chloride (86 μL, 1.21 mmol) was added dropwise to methanol (0.5 mL) and stirred for 10 minutes then added to tert-butyl 4-{3-[4-(methylthio)benzyl]-1,2,4-oxadiazol-5-yl}piperidine-1-carboxylate (237 mg, 0.61 mmol) in MeOH (5 mL) and the mixture heated to 60° C. for 1 hour and the solvents evaporated to give a the title compound as a yellow powder, (199 mg, 100%); MS: 290 (MH+).

Method F 4-(3-Methyl-[1,2,4]oxadiazol-5-yl)-piperidine hydrochloride

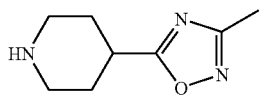

Step 1: Hydroxylamine (50% w/v solution in water, 20 mL, 10.0 g) was added to acetonitrile (19.0 mL, 14.9 g, 364 mmol, 1.2 equivalents) and the mixture stirred at ambient temperature for 64 hours with the formation of a fine white precipitate, which was filtered and washed with water and diethylether, dried, and combined with the evaporated filtrates and recrystallised from hot methanol (50 mL) and dried to give N'-hydroxyethanimidamide as white needles; NMR: 1.63(3H, s), 5.32(2H, s), 8.67(1H, s).

Step 2: 1-(tert-Butoxycarbonyl)piperidine-4-carboxylic acid (5.00 g, 21.83 mmol), 1-hydroxybenzotriazole (2.95 g, 21.83 mmol) and N-methylmorpholine (4.8 mL, 43.67 mmol) were dissolved in dichloromethane (100 mL), under argon, and (3-dimethylaminopropyl)carbodiimide hydrochloride (4.60 g, 24.0 mmol) and N'-hydroxyethanimidamide (1.62 g, 21.83 mmol) were added. The mixture was stirred at room temperature overnight then water (50 mL) was added and the mixture stirred for 30 minutes. The organics were separated, dried and the solvent evaporated to give a yellow oil which was redissolved in 1,4-dioxane (100 mL) and heated to 100° C. for 3 hours, cooled and the solvent evaporated to give crude tert-butyl 4-(3-methyl-1,2,4-oxadiazol-5-yl)piperidine-1-carboxylate as a brown oil (5.74 g, 98.5%).

Step 3: Crude tert-butyl 4-(3-methyl-1,2,4-oxadiazol-5-yl)piperidine-1-carboxylate (5.73 g, 21.3 mmol) was dissolved in MeOH (100 mL) and a premixed solution of acetyl chloride (1.53 mL, 42.8 mmol) in MeOH (10 mL) was added and the mixture heated to 60° C. for 1 hour, then the solvents were evaporated and the resultant gum triturated with dichloromethane/diethyl ether (1:1) to give a cream solid which was filtered, washed with diethyl ether and dried, to give the title compound as a solid (1.98 g, 55% yield); MS: 168 (MH+).

Method G

4-[2-(4-Chloro-benzyl)-2H-tetrazol-5-yl]-piperidine

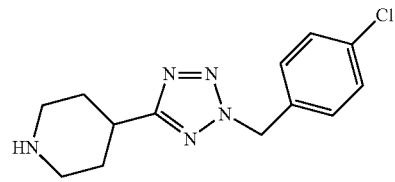

Step 1: Isonipecotamide (10 g) was added portionwise over 15 minutes to phosphorous oxychloride at 0° C. The resulting mixture was refluxed for 2 hours and then cooled and poured slowly onto water keeping the temperature below 20° C. The resulting mixture was neutralised using concentrated potassium hydroxide and extracted with dichloromethane. The organics were dried (MgSO$_4$) and evaporated to give 4-cyanopiperidine as an oil, which was used without further purification.

Step 2: The crude 4-cyanopiperidine was dissolved in methanol (50 mL) and di-tert-butyldicarbonate (17 g) was added. The resulting mixture was stirred for 5 hours. The mixture was concentrated to an oil which was purified by column chromatography eluting with an ethyl acetate/isohexane gradient (10:90 to 40:60 v/v) to give tert-butyl 4-cyanopiperidine-1-carboxylate (9.25 g) as an oil; NMR (CDCl$_3$): 1.45 (s, 9H), 1.85 9m, 4H), 2.8 (m, 1H), 3.4 (m, 2H), 3.7 (m, 2H).

Step 3: A mixture of tert-butyl 4-cyanopiperidine-1-carboxylate (2.1 g), sodium azide (1.95 g) and ammonium chloride (1.6 g) in dimethylformamide was heated to 100° C. for 18 hours. The mixture was cooled and partitioned between 1N HCl and dichloromethane. The organic layer was washed with water, dried (MgSO$_4$) and evaporated to give a gum which was purified by column chromatography eluting with MeOH/dichloromethane (1:99) to give tert-butyl 4-(2H-tetrazol-5-yl)piperidine-1-carboxylate (1.31 g); NMR (CDCl₃): 1.5 (s, 9H), 1.9 (m, 2H), 2.15 (m, 2H), 3.0 (m, 2H), 3.3 (m, 1H), 4.2 (m, 2H).

Step 4: To a solution of tert-butyl 4-(2H-tetrazol-5-yl)piperidine-1-carboxylate (873 mg) in dimethylformamide (5 mL), cooled to 5° C., was added sodium hydride (165 mg 60% dispersion in oil). The resulting mixture was stirred for 30 minutes before the addition of a solution of 4-chlorobenzyl bromide (780 mg) in dimethylformamide (1 mL). The mixture was allowed to warm to room temperature and stirred for a further 3 hours. The mixture was poured onto water and extracted with ethyl acetate. The extract was then dried (MgSO₄) and evaporated to a gum. Purification by column chromatography eluting with a slow gradient of ethyl acetate/isohexane (10:90 to 70:30) gave firstly tert-butyl 4-[2-(4-chlorobenzyl)-2H-tetrazole-5-ylpiperidine-1-carboxylate (539 mg;) NMR (CDCl₃): 1.5 (s, 9H), 1.8 (m, 2H), 2.05 (m, 2H), 2.95 (m, 1H), 3.1 (m, 2H), 4.1 (m, 2H), 5.7 (s, 2H), 7.35 (d, 2H), 7.4 (d, 2H); followed by tert-butyl 4-[1-(4-chlorobenzyl)-2H-tetrazole-5-ylpiperidine-1-carboxylate (488 mg); NMR (CDCl₃) 1.5 (s, 9H), 1.7 (m, 2H), 1.9 (m, 2H), 2.9 (m, 3H), 4.15 (m, 2H), 5.55 (s, 2H), 7.15 (d, 2H), 7.4 (d, 2H).

Step 5: To a solution of tert-butyl 4-[2-(4-chlorobenzyl)-2H-tetrazole-5-ylpiperidine-1-carboxylate (532 mg) in dichloromethane (4 mL) was added trifluoroacetic acid (4 mL) and the resulting mixture was stirred for 3 hours. The mixture was concentrated and azeotroped with 7N NH₃ in methanol. The resulting gum was purified by column chromatography eluting with 7N NH₃ in methanol/dichloromethane (1:99 to 5:95 v/v) to give 4-[2-(4-chlorobenzyl)-2H-tetrazol-5-yl]piperidine (328 mg); NMR (CDCl₃): 1.8 (m, 2H), 2.1 (m, 2H), 2.8 (m, 2H), 3.1 (m, 1H), 3.2 (m, 2H), 5.7 (s, 2H), 7.3-7.4 (dd, 4H).

Method H

4-[2-(4-Methanesulfonyl-benzyl)-2H-tetrazol-5-yl]-piperidine

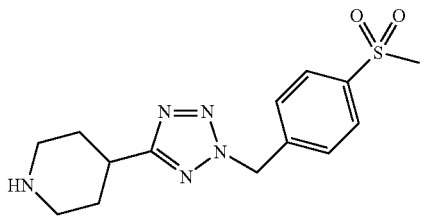

This was prepared from 4-methanesulphonylbenzyl bromide and tert-butyl 4-(2H-tetrazol-5-yl)piperidine-1-carboxylate using a similar method to that used to prepare 4-[2-(4-chloro-benzyl)-2H-tetrazol-5-yl]-piperidine (Method G, Steps 4 and 5); NMR (CDCl₃): 1.8 (m, 2H), 2.05 (m, 2H), 2.8 (m, 2H), 3.05 (s, 3H), 3.1 (m, 1H), 3.2 (m, 2H), 5.89 (s, 2H), 7.55 (d, 2H), 7.95 (d, 2H).

Method I 4-(5-Benzyl-2-methyl-2H-pyrazol-3-yl)-piperidine

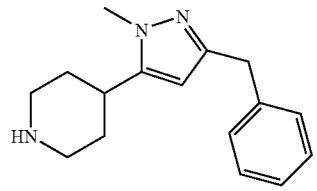

Step 1: To a stirred solution of methyl magnesium bromide (3.0M in THF, 76 mL) was added, via cannula over 10 minutes, a solution of 4-cyano-piperidine-1-carboxylic acid tert-butyl ester (12.00 g; prepared as described in *Chem. Pharm. Bull.*, 2001, 49, 822) in anhydrous THF (120 mL). The green cloudy solution was then left to stir overnight at room temperature. The reaction was quenched by cannula transfer into a rapidly stirred solution of saturated aqueous ammonium chloride (500 mL), which was then stirred for 15 minutes before neutralisation to pH 7 by the addition of 1M aqueous HCl. The reaction mixture was then extracted into Et₂O (700 mL1) and washed with 10% aqueous citric acid followed by brine. The organic extracts were then dried over magnesium sulfate and filtered under suction before evaporation of solvents under reduced pressure to give the crude product as a mobile yellow oil (7.00 g). This was purified by column chromatography on silica gel, eluting with an increasingly polar gradient of Et₂O in DCM as eluent. Evaporation of solvents under reduced pressure gave the desired product as a clear colourless oil (4.00 g); NMR (CDCl₃): 1.45 (s, 9H), 1.52 (m, 2H), 1.83 (br d, 2H), 2.16 (s, 3H), 2.45 (tt, 1H), 2.79 (br t, 2H), 4.10 (br d, 2H).

Step 2: 4-Acetyl-piperidine-1-carboxylic acid tert-butyl ester (1.00 g) was dissolved in anhydrous THF (6 mL) and cooled to 0° C. To this was added a solution of lithium hexamethyldisilazane (1.0M in hexanes; 4.84 mL). This was left to stir at 0° C. for 10 minutes before addition of a THF solution (2 mL) of methyl phenylacetate (0.661 g). The reaction mixture was left to stir for a total of 4 hours before being quenched by the addition of 1M aqueous HCl (50 mL). The reaction mixture was extracted with Et₂O (3×75 mL) then the combined organic extracts were dried over magnesium sulfate and filtered. Evaporation of solvents under reduced pressure gave a thick yellow oil which was purified by column chromatography on silica gel, using an increasingly polar gradient of Et₂O in DCM as eluent. Evaporation of solvents under reduced pressure gave the desired 4-(3-oxo-4-phenyl-butyryl)-piperidine-1-carboxylic acid tert-butyl ester as a clear oil (0.225 g); NMR (CDCl₃): 1.45 (s, 9H), 1.54 (m, 2H), 1.76 (d, 2H), 2.28 (tt, 1H), 2.71 (br t, 2H), 3.61 (s, 2H), 4.12 (br d, 2H), 5.44 (s, 1H), 7.12-7.36 (m, 5H), 15.30 (s, 1H); MS: 344 (M−1⁻).

Step 3: 4-(3-Oxo-4-phenyl-butyryl)-piperidine-1-carboxylic acid tert-butyl ester (0.118 g) was dissolved in MeOH (4 mL) and added to a refluxing solution of methyl hydrazine (0.019 g) in methanol (2 mL). After 45 minutes at reflux the reaction mixture was cooled to room temperature and solvents evaporated under reduced pressure to give the crude product as a clear oil which was purified by column chromatography on silica using Et₂O as eluent to give 4-(5-benzyl-2-methyl-2H-pyrazol-3-yl)-piperidine-1-carboxylic acid tert-butyl ester (0.032 g) as a clear oil; NMR (CDCl₃): 1.46 (s, 9H), 1.46-1.54 (m, 2H), 1.82 (br d, 2H), 2.64 (tt, 1H), 2.78 (br t, 2H), 3.77 (s, 3H), 3.90 (s, 2H), 4.18 (br d, 2H), 5.72 (s, 1H), 7.16-7.29 (m, 5H); MS: 356 (MH+).

Step 4: 4-(5-Benzyl-2-methyl-2H-pyrazol-3-yl)-piperidine-1-carboxylic acid tert-butyl ester (0.032 g) was dissolved in a 25% v/v solution of trifluoroacetic acid in DCM (7 mL) and stirred for 30 minutes. The solvents were then evaporated under reduced pressure to give a clear oil which was purified by column chromatography on SCX-2 stationary phase using a gradient of DCM up to 50% 7N NH₃ in MeOH in DCM as eluent. Evaporation of solvent under reduced pressure gave the title compound as a clear oil (0.018 g); NMR(CDCl₃): 1.50-1.60 (qd, 2H), 1.85 (br d, 2H), 2.64 (tt, 1H), 2.66-2.76 (qd, 2H), 3.17 (br d, 2H), 3.76 (s, 3H), 3.91 (s, 2H), 5.76 (s, 1H), 7.16-7.20 (m, 1H), 7.24-7.30 (m 4H); MS: 256 (MH+).

Preparation of 4-[2-ethyl-5-(4-fluoro-benzyl)-2H-pyrazol-3-yl]-piperidine

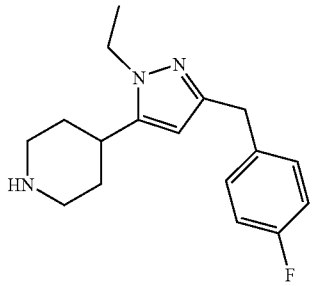

This material was prepared in a fashion similar to that described in Method I except that the methyl phenylacetate used in Step 2 was substituted with methyl (4-fluorophenyl)acetate, to give 4-[4-(4-fluoro-phenyl)-3-oxo-butyryl]-piperidine-1-carboxylic acid tert-butyl ester [NMR (CDCl₃): 1.45 (s, 9H), 1.50-1.60 (m, 2H), 1.74-1.80 (br d, 2H), 2.24-2.34 (tt, 1H), 2.68-2.77 (br t, 2H), 3.58 (s, 2H), 4.07-4.18 (br m, 2H), 5.44 (s, 1H), 6.99-7.05 (m, 2H), 7.16-7.22 (m, 2H), 15.30 (s, 1H); MS: 362 (M−1⁻)], and the methyl hydrazine used in Step 3 was substituted with ethyl hydrazine oxalate and diisopropylethylamine (in equimolar ratio) to give 4-[2-ethyl-5-(4-fluoro-benzyl)-2H-pyrazol-3-yl]-piperidine-1-carboxylic acid tert-butyl ester [NMR (CDCl₃): 1.41-1.45 (t, 3H), 1.46 (s, 9H), 1.49-1.54 (m, 2H), 1.79-1.83 (br d, 2H), 2.60-2.69 (tt, 1H), 2.74-2.82 (br t, 2H), 3.89 (s, 2H), 4.03-4.08 (q, 2H), 4.15-4.25 (br d, 2H), 5.68 (s, 1H), 6.93-6.98 (m, 2H), 7.17-7.21 (m, 2H); MS: 388 (MH+)], and subsequent removal of the protecting group gave the title compound as a clear gum (0.042 g); MS: 288 (MH+).

Method J (R)-3-(4-Methanesulfonyl-phenyl)-3-thiophen-2-yl-propionaldehyde

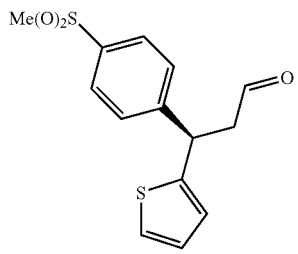

Step 1: Preparation of (4S,5R)-1,5-dimethyl-4-phenyl-3-(3-thiophen-2-yl-acryloyl)-imidazolidin-2-one

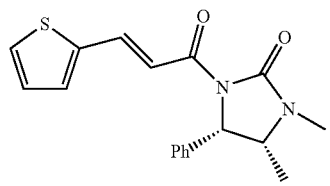

(2-Thiophene)cinnamic acid (1.22 g, 7.88 mmol) was suspended in dichloromethane (10 mL) and oxalyl chloride (0.86 mL, 9.86 mmol) was added dropwise. After stirring for 2 h, the acid chloride was concentrated in vacuo and azeotroped with toluene to dryness. (4S,5R)-1,5-Dimethylphenyl-imidazolidin-2-one (1.25 g, 6.57 mmol) and DIPEA (2.52 mL, 14.5 mmol) were premixed in dichloromethane (3 mL) and were added to the acid chloride as one portion. This was then stirred overnight. Aqueous workup (washing with water, then brine and concentrating) followed by column chromatography (hexane to dichloromethane) gave the sub-titled compound (1.13 g, 44%) as a yellow oil; NMR (CDCl₃): 0.85 (d, 3H), 2.90 (s, 3H), 3.95 (m, 1H), 5.42 (d, 1H), 7.03 (m, 1H), 7.28 (m, 7H), 7.90 (d, 1H), 8.00 (d, 1H); LCMS: 327 (MH+).

Step 2: Preparation of (4R,5S)-1-[(R)-3-(4-methanesulfonyl-phenyl)-3-thiophen-2-yl-propionyl]-3,4-dimethyl-5-phenyl-imidazolidin-2-one

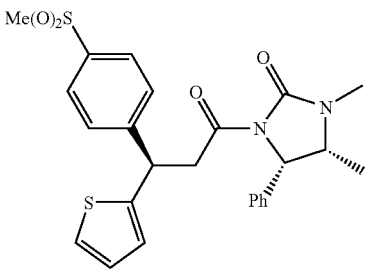

Copper (I) iodide (1.3 g, 6.89 mmol) was suspended in tetrahydrofuran (10 mL) under argon and TMEDA (1.14 mL, 7.58 mmol) was added as a single portion. After stirring for 10 min the solution was cooled to −78° C. and 4-thioanisyl phenylmagnesium bromide (14 mL, 6.89 mmol) was added dropwise. The resulting solution was then stirred for a further 30 min at −78° C. To this mixture was then added slowly a mixture of (4S,5R)-1,5-dimethyl-4-phenyl-3-(3-thiophen-2-yl-acryloyl)-imidazolidin-2-one (1.13 g) and dibutylboron triflate (4.2 mL, 4.14 mmol) in tetrahydrofuran (10 mL) at −78° C. and then the resulting mixture was stirred and allowed to warm to room temperature overnight. The reaction was then quenched with saturated aqueous ammonium chloride and washed with concentrated tetrasodium EDTA solution. The organics were then separated, concentrated and redissolved in ethyl acetate (100 mL). meta-Chloroperbenzoic acid (1.7 g, 6.9 mmol) was added as a single portion and the solution stirred for 2 h. This was then quenched with 2M aqueous sodium hydroxide solution and the resulting precipitate collected by filtration. This gave the sub-titled compound (1.06 g, 64%) as a white solid; NMR (CDCl₃): 0.80 (d, 3H), 2.83 (s, 3H), 3.00 (s, 3H), 3.72 (dd, 1H), 3.85 (m, 1H), 4.05 (dd, 1H), 4.95 (t, 1H), 5.22 (d, 1H), 6.90 (m, 3H), 7.21 (m, 5H), 7.44 (d, 2H), 7.79 (d, 2H); LCMS: 483 (MH+).

Step 3. Preparation of Title Compound (4R,5S)-1-[(R)-3-(4-Methanesulfonyl-phenyl)-3-thiophen-2-yl-propionyl]-3,4-dimethyl-5-phenyl-imidazolidin-2-one (1.05 g, 2.18 mmol) was dissolved in dichloromethane (40 mL) under argon and the solution was cooled to −78° C. DIBAL solution (7 mL, 6.53 mmol) was then added dropwise and the solution stirred at −78° C. for a further 2 h. Crushed Glauber's salt (7 g) was then added and the reaction stirred vigorously at room temperature for 1 h. This was then filtered and stirred with basic alumina (7 g) for 4 h. Filtration and concentration gave the title compound (0.25 g, 38%) as a colourless oil; NMR (CDCl₃): 3.05 (s, 3H), 3.24 (m, 2H), 4.96 (t, 1H), 6.85 (m, 1H), 6.93 (m, 1H), 7.20 (m, 1H), 7.48 (d, 2H), 7.90 (d, 2H), 9.76 (s, 1H).

Method K (R)-3-(4-Methanesulfonyl-phenyl)-3-thiophen-3-yl-propionaldehyde

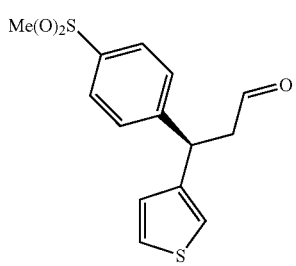

This was prepared from (3-thiophene)cinnamic acid using a similar sequence of reactions used to prepare (R)-3-(4-Methanesulfonyl-phenyl)-3-thiophen-2-yl-propionaldehyde (Method J); NMR (CDCl₃): 3.03 (s, 3H), 3.20 (m, 2H), 4.79 (t, 1H), 6.85 (m, 1H), 7.00 (m, 1H), 7.25 (m, 1H), 7.40 (d, 2H), 7.85 (d, 2H), 9.75 (s, 1H).

Method L (R)-3-(4-Methanesulfonyl-phenyl)-3-(5-chlorothiophen-2-yl)-propionaldehyde

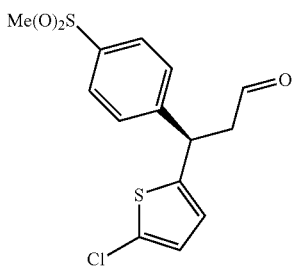

This was prepared from (2-[5-chlorothiophene])cinnamic acid using a similar sequence of reactions used to prepare (R)-3-(4-Methanesulfonyl-phenyl)-3-thiophen-2-yl-propionaldehyde (Method J); NMR (CDCl₃): 3.05 (s, 3H), 3.20 (m, 2H), 4.82 (t, 1H), 6.62 (m, 1H), 6.72 (m, 1H), 7.45 (d, 2H), 7.89 (d, 2H), 9.73 (s, 1H).

Method M (R)-3-(4-Methanesulfonyl-phenyl)-3-(4-chlorothiophen-2-yl)-propionaldehyde

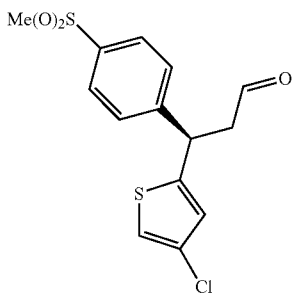

This was prepared from (2-[4-chlorothiophene])cinnamic acid using a similar sequence of reactions used to prepare (R)-3-(4-Methanesulfonyl-phenyl)-3-thiophen-2-yl-propionaldehyde (Method J); NMR (CDCl₃): 3.04 (s, 3H), 3.23 (m, 2H), 4.86 (t, 1H), 6.70 (m, 1H), 6.95 (m, 1H), 7.45 (d, 2H), 7.87 (d, 2H), 9.75 (s, 1H).

Method N (S)-3-Phenyl-3-(4-methanesulfonylphenyl)propionaldehyde

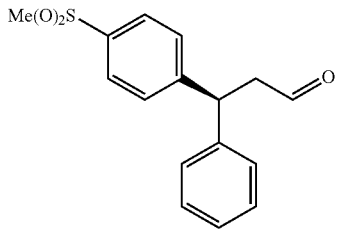

35

Step 1: Preparation of (4S,5R)-1-[(S)-3-(4-methane-sulfonyl-phenyl)-3-phenyl-propionyl]-3,4-dimethyl-5-phenyl-imidazolidin-2-one

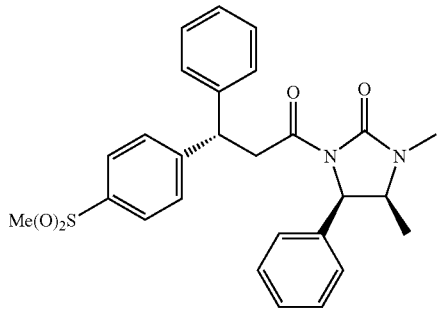

To a mixture of copper (I) iodide (960 mg, 5.0 mmol) and THF (20 mL) was added N,N,N',N'-tetramethylethylenediamine (0.83 mL, 5.5 mmol) and the resulting mixture was stirred at room temperature for 10 min. then cooled to −78° C. Phenylmagnesium bromide (5.0 mL, 1M in THF, 5.0 mmol) was added and the resulting mixture stirred at −78° C. for 15 min. A solution of di-n-butylboron triflate (3.0 mL, 1M in diethyl ether, 3.0 mmol) and (E)-(4S,5R)-1-(3-[4-methanesulfonylphenyl]acryloyl)-3,4-dimethyl-5-phenyl-imidazolidin-2-one (Method D, 1.0 g, 2.51 mmol) in THF (15 mL) was added and the resulting mixture was stirred whilst allowing to warm to room temperature for 18 h. The reaction mixture was washed with saturated aqueous ammonium chloride, water and brine, dried (MgSO$_4$) and evaporated. The residue was purified by eluting through a 20 g Bond Elut with gradient of isohexane to ethyl acetate giving the sub-titled compound (1.49 g, 100%); NMR (CDCl$_3$): 0.78 (d, 3H), 2.82 (s, 3H), 3.00 (s, 3H), 3.78 (dd, 1H), 3.80 (m, 1H), 3.98 (dd, 1H), 4.72 (m, 1H), 5.19 (d, 1H), 6.99 (m, 2H), 7.22 (m, 8H), 7.48 (d, 2H), 7.79 (d, 2H); MS: 477 (MH+).

Step 2: Preparation of (S)-3-phenyl-3-(4-methane-sulfonylphenyl)propan-1-ol

To a solution of (4S,5R)-1-[(S)-3-(4-methanesulfonyl-phenyl)-3-phenyl-propionyl]-3,4-dimethyl-5-phenyl-imidazolidin-2-one (846 mg, 1.78 mmol) in THF (20 mL) at 0° C. was added lithium aluminium hydride (3.6 mL, 1M in THF, 3.6 mmol) and the resulting mixture was stirred for 15 min. The reaction was quenched by the addition of 2M aqueous sodium hydroxide. The phases were separated and the organic phase pre-absorbed onto a Bond Elut and eluted with a gradient of isohexane to ethyl acetate giving the sub-titled compound as a white solid (285 mg, 55%); NMR (CDCl$_3$): 1.63 (br s, 1H), 2.33 (m, 2H), 3.00 (s, 3H), 3.59 (t, 2H), 4.28 (t, 1H), 7.23 (m, 5H), 7.43 (d, 2H), 7.82 (d, 2H).

Step 3: Preparation of the Title Compound

To a solution of (S)-3-phenyl-3-(4-methanesulfonylphe-nyl)propan-1-ol (244 mg, 0.84 mmol) in DCM (5 mL) was added Dess-Martin periodinane (392 mg, 0.92 mmol) and the resulting mixture was stirred at room temperature for 1.5 h. The mixture was washed with 2M aqueous sodium hydroxide (2×10 mL), dried and evaporated to give the title compound.

36

Method O (R)-3-(3-Fluorophenyl)-3-(4-methanesulfonylphe-nyl)propionaldehdye

This was prepared from (4S,5R)-1-(3-[4-methanesulfo-nylphenyl]acryloyl)-3,4 dimethyl-5-phenyl-imidazolidin-2-one and 3-fluorophenylmagnesium bromide using a method similar to that used to prepare (S)-3-phenyl-3-(4-methane-sulfonyl-phenyl)propionaldehyde from phenylmagnesium bromide (Method N); NMR (CDCl$_3$): 3.01 (s, 3H), 3.24 (d, 2H), 4.73 (t, 1H), 6.91 (m, 2H), 6.99 (m, 1H), 7.28 (m, 2H), 7.42 (d, 2H), 7.87 (d, 2H), 9.76 (s, 1H).

Method P (R)-3-(3,5-Difluorophenyl)-3-(4-methanesulfo-nylphenyl)propionaldehyde

This was prepared from (4S,5R)-1-(3-[4-methanesulfo-nylphenyl]acryloyl)-3,4-dimethyl-5-phenyl-imidazolidin-2-one and 3,5-difluorophenylmagnesium bromide using a method similar to that used to prepare (S)-3-phenyl-3-(4-methanesulfonyl-phenyl)propionaldehyde from phenylmag-nesium bromide (Method N).

Method Q (R)-3-(3-Chloro-5-fluorophenyl)-3-(4-methanesulfo-nylohenyl)propionaldehyde This was prepared from (4S,5R)-1-(3-[4-methanesulfo-nylphenyl]acryloyl)-3,4-dimethyl-5-phenyl-imidazolidin-2-one and 3-chluoro-5-fluorophenylmagnesium bromide using a method similar to that used to prepare (S)-3-phenyl-3-(4-methanesulfonyl-phenyl)propionaldehyde from phenylmag-nesium bromide (Method N).

Method R

4-[2-(4-Chlorobenzyl)-1,3-thiazol-4-yl]piperidine

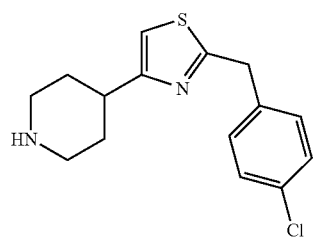

Step 1: To a solution of 1-[(allyloxy)carbonyl]piperidine-4-carboxylic acid (7 g) in dichloromethane (60 ml) and DMF (4 drops), cooled to 5° C., was added oxalyl chloride (6 ml). The reaction mixture was stirred for 2 hours at room temperature, evaporated and azeotroped with anhydrous THF. The resulting residue was dissolved in anhydrous THF (100 ml), cooled to 5° C., and trimethylsilyldiazomethane (45.5 ml of 2M solution in THF) was added dropwise. The resulting mixture was stirred at room temperature for 1 hour. Diethyl ether (100 ml) was added and the organics was washed with saturated sodium bicarbonate (50 ml). The organics was separated, dried and evaporated. The residue was dissolved in diethyl ether (60 ml), cooled to 5° C. and HBr in acetic acid (6.55 ml, 33% solution) was added. The resulting mixture was stirred for 1 hour. The reaction was basified with saturated sodium bicarbonate and extracted with diethyl ether (×2). The organics were dried and evaporated to dryness. The residue was purified by chromatography on silica eluting with a gradient of isohexane to ethyl acetate hexane/isohexane (2:5) to give allyl 4-(bromoacetyl)piperidine-1-carboxylate as an oil. Yield 4.92 g. NMR (CDCl$_3$): 1.7 (m, 2H), 1.9 (m, 2H), 2.5 (m, 1H), 2.95 (m, 2H), 3.7 (s, 3H), 4.1 (m, 2H), 4.6 (m, 2H), 5.3 (m, 2H), 5.95 (m, 1H).

Step 2: A mixture of allyl 4-(bromoacetyl)piperidine-1-carboxylate (547 mg) and 2-(4-chlorophenyl)ethanethioamide (366 mg) in ethanol (15 ml) was refluxed for 5 hours. The reaction mixture was evaporated to dryness and the residue was purified by chromatography on silica eluting with methanol/dichloromethane (2:98) to give allyl 4-[2-(4-chlorobenzyl)-1,3-thiazol-4-yl]piperidine-1-carboxylate. Yield 698 mg. NMR (CDCl$_3$): 1.65 (m, 2H), 2.25 (m, 2H), 2.95 (m, 2H), 3.2 (m, 1H), 4.3 (m, 2H), 4.55 (m, 4H), 5.3 (m, 2H), 6.0 (m, 1H), 6.95 (s, 1H), 7.35 (m, 4H).

Step 3: To a solution of allyl 4-[2-(4-chlorobenzyl)-1,3-thiazol-4-yl]piperidine-1-carboxylate (692 mg) in anhydrous THF (20 ml) was added dimedone (2.06 g) followed by Pd(PPh$_3$)$_4$ (201 mg) and the resulting mixture was stirred at room temperature for 4 hours. A further portion of dimedone (1.03 g) and Pd(PPh$_3$)$_4$ (100 Mg) was added and the mixture was stirred for a further 18 hours. The reaction mixture was partitioned between 1N sodium hydroxide (50 ml) and ethyl acetate (100 ml). The organics were separated, dried and evaporated to dryness. The residue was purified by column chromatography on SCX-2 stationary phase using a gradient of DCM up to 50% 7N NH$_3$ in MeOH in dichloromethane as eluent to give 4-[2-(4-chlorobenzyl)-1,3-thiazol-4-yl]piperidine as a solid. Yield 162 mg). NMR (CDCl$_3$): 1.8 (m, 2H), 2.2 (m, 2H), 2.4 (bs, 1H), 2.8-3.0 (m, 3H), 3.3 (m, 2H), 4.4 (s, 2H), 7.4 (m, 5H).

Method S 4-(2-Methyl-2H-tetrazol-5-yl)-piperidine

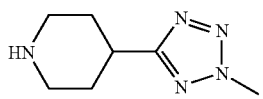

To a solution of tert-butyl 4-(2H-tetrazol-5-yl)piperidine-1-carboxylate (CAS 91419-58-8) (0.98 g, 3.89 mmol) and triphenylphosphine (3.06 g) in THF under a blanket of Ar was added the diisopropyl azodicarboxylate (2.30 ml) and the mixture stirred for 10 minutes. Methanol (473 µl) was added and the reaction was stirred for 18 hours and then the solution was concentrated in vacuo. The residue was purified on silica using a 90 g Biotage cartridge and a gradient elution of 25 to 35% ethyl acetate in hexanes. This semi-pure mixture was partially dissolved in a 4M HCl in dioxane solution and stirred for 1 hour, then concentrated in vacuo. The residue was partially dissolved in DCM (40 ml) and triethylamine (162 µl) and MP-Carbonate (4.17 g, loading 2.8 mmol/g) added and slurry stirred for 64 hours. The resin was filtered off and washed with a 10% solution of methanol in DCM and the filtrate was concentrated in vacuo. The residue was purified by column chromatography on SCX-2 stationary phase using methanol and then a 1M ammonia in methanol solution. Evaporation of the solvent under reduced pressure gave the title compound as a yellow solid (0.502 g); NMR (CDCl$_3$): 1.78 (2H, m), 2.06 (2H, d), 2.77 (2H, m), 3.08 (1H, m), 3.19 (2H, d), 3.08 (3H, s).

Method T

5-Ethyl-3-piperidin-4-ylimidazolidine-2,4-dione

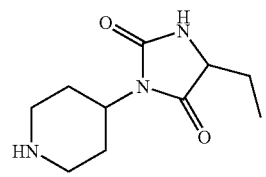

Step 1: To a solution of 5-ethylimidazoline-2,4-dione (1 g) in DMF (40 ml) was added potassium carbonate (2.16 g) followed by tert-butyl 4-[(methylsulfonyl)oxy]piperidine-1-carboxylate (2.18 g) and the resulting mixture was heated to 100° C. for 18 hours. The reaction mixture was concentrated under reduced pressure and then was partitioned between dichloromethane and water. The organic layer was collected, dried and evaporated to dryness. The residue was purified by chromatography on silica eluting with a gradient of isohexane to ethyl acetate/isohexane (1:1) to give tert-butyl 4(4-ethyl-2,5-dioxoimidazolidin-1-yl)piperidine-1-carboxylate as a solid. Yield 1.12 g. NMR (CDCl$_3$): 0.95 (t, 3H), 1.5 (s, 9H), 1.9 (m, 2H), 2.35 (m, 2H), 2.7 (m, 2H), 3.8-4.0 (m, 3H), 4.1 (q, 2H), 5.6 (bs, 1H).

Step 2: To a suspension of tert-butyl 4-(4-ethyl-2,5-dioxoimidazolidin-1-yl)piperidine-1-carboxylate (1.12 g) in dioxane (10 ml) was added a solution of 4M HCl in dioxane (10 ml) and the resulting mixture was stirred for 1 hour. Diethyl ether (20 ml) was added and the mixture was filtered and washed with diethyl ether to give 5-ethyl-3-piperidin-4-ylimidazolidine-2,4-dione. Yield 687 mg. MS 212 MH$^+$ In a similar manner but using 5-phenylimidazoline-2,4-dione was prepared 5-phenyl-3-piperidin-4-ylimidazolidine-2,4-dione. MS 260 MH$^+$ In a similar manner but using using 5-methylimidazoline-2,4-dione was prepared 5-methyl-3-piperidin-4-ylimidazolidine-2,4-dione. MS 198 MH$^+$ Method U 4-(4H-1,2,4-Triazol-4-yl)piperidine

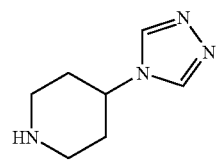

Step 1: To a solution of 1,2-bis[(dimethylamino)methylene]hydrazine (660 mg) in toluene (10 ml) was added 1-benzylpiperidin-4-amine (0.8 ml) and p-toluenesulfonic acid (75 mg) and the resulting mixture was stirred at room temperature for 18 hours. The reaction mixture was refluxed for 8 hours and then evaporated to dryness. The residue was purified by chromatography on silica eluting with a gradient of methanol/ethyl acetate to give 1-benzyl-4-(4H-1,2,4-triazol-4-yl)piperidine. Yield 220 mgs. NMR (d6 DMSO): 2.0 (m, 4H), 2.1 (m, 2H), 2.9 (m, 2H), 3.5 (s, 2H), 4.2 9m, 1H), 7.35 (m, 5H), 8.65 (s, 2H).

Step 2: To a solution of 1-benzyl-4-(4H-1,2,4-triazol-4-yl)piperidine (200 mg) in ethanol (10 ml) was added palladium hydroxide (170 mg) followed by ammonium formate 9262 mg). The resulting mixture was refluxed for 1 hour. The mixture was cooled, filtered through Celite and evaporated to dryness to give 4-(4H-1,2,4-triazolyl)piperidine as a white solid. Yield 100 mg. NMR (d6 DMSO) 1.75 (m, 2H), 1.95 (m, 2H), 2.6 (m, 2H), 3.05 (m, 2H), 3.3 (bs, 1H), 4.2 (m, 1H), 8.6 (s, 2H).

Method V 4-(3,5-Dimethyl-4H-1,2,4-triazol-4-yl)piperidine

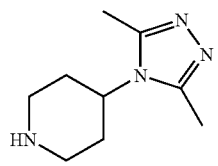

Step 1: To a solution of 1-benzylpiperidin-4-amine (10 g) in dichloromethane (80 ml), cooled to 5° C., was added pyridine (5.1 ml) followed by acetyl chloride (4.5 ml) and the resulting mixture was stirred for 5 hours. The reaction mixture was washed with 1N NaOH (×2) and then the organic layers were dried and evaporated to dryness to give a solid which was recrystallised from ethyl acetate to give N-(1-benzylpiperidin-4-yl)acetamide. Yield 8.8 g. NMR (d6 DMSO): 1.4 (m, 2H), 1.7 (m, 2H), 1.8 (s, 3H), 2.0 (m, 2H), 2.75 (m, 2H), 3.45 (s, 2H), 3.55 (m, 1H), 7.3 (m, 5H), 7.75 (d, 1H).

Step 2: To a solution of N-(1-benzylpiperidin-4-yl)acetamide (8.8 g) in chloroform (30 ml), cooled to 5° C. was added dropwise phosphorous oxychloride (10.6 ml) keeping the temperature below 5° C. The resulting mixture was stirred at 5° C. for 18 hours. The reaction mixture was concentrated and azeotroped with toluene. The residue was redissolved in chloroform (30 ml) and acetic hydrazide (4.21 g) was added. The resulting mixture was refluxed for 18 hours. The reaction mixture was cooled, basified with saturated sodium bicarbonate, extracted with dichloromethane (×2), dried and evaporated. The residue was dissolved in 7M HCl and refluxed for 8 hours. The reaction mixture was cooled, basified with aqueous potassium carbonate, extracted with dichloromethane (×2), dried and evaporated. The residue was purified by chromatography eluting with ethyl acetate/isohexane (20:80) to give 1-benzyl-4-(4H-1,2,4-triazol-4-yl)piperidine. Yield 1 g. NMR (d6 DMSO): 1.8 (m, 2H), 2.1 (m, 4H), 2.4 (s, 6H), 2.95 (m, 2H), 3.55 (s, 2H), 3.95 (m, 1H), 7.35 (m, 5H).

Step 3: In a similar manner to Method U step 2 was prepared 4-(3,5-dimethyl-4H-1,2,4-triazol-4-yl)piperidine. NMR (d6 DMSO): 1.75 (m, 2H), 1.9 (m, 2H), 2.4 (s, 6H), 2.6 (m, 2H), 3.05 (m, 2H), 4.0 (m, 1H).

Method W

Preparation of 3-(3-isopropyl-5-methyl-4H-1,2,4-triazol-4-yl)-exo-8-azabicyclo[3.2.1]octane

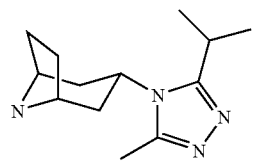

Step 1: Preparation of 8-benzylbicyclo[3.2.1.]octan-3-one

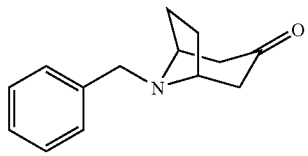

A solution of 2,5-dimethoxytetrahydrofuran (22.2 ml) in 0.1M HCl was refluxed for 1 hour and then cooled to 0° C. 1.3-Acetonedicarboxylic acid (25 g), benzylamine (15.6 ml) and 10% sodium acetate (95 ml) was added in one portion and the resulting mixture was stirred at room temperature for 1 hour and then heated to 50° C. for 5 hours. The reaction mixture was cooled, basified with 2M sodium hydroxide, extracted with dichloromethane and washed with water. The organics were extracted with 1M hydrochloric acid and washed with dichloromethane. The aqueous layer was basified with 2M sodium hydroxide and extracted with ethyl acetate (3×100 ml). The organic extracts were dried and evaporated to dryness to give the title compound as a brown oil which was used without further purification. Yield 13.66 g. MS 216 MH+.

Step 2: Preparation of 8-benzylbicyclo[3.2.1.]octan-3-one-O-methyloxime

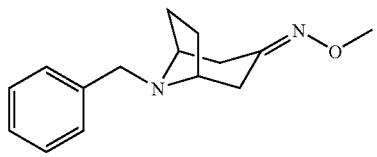

To a solution of 8-benzylbicyclo[3.2.1.]octan-3-one (13.66 g) in ethanol (250 ml) was added pyridine (5.69 ml) followed by hydroxylamine hydrochloride (4.85 g) and the resulting mixture was refluxed for 18 hours. The reaction mixture was allowed to cool to room temperature and then partitioned between water and dichloromethane. The organic layer was dried and evaporated to give the title compound as a brown solid which was used without further purification. Yield 10.79 g. MS 231 MH+.

Step 3: Preparation of 8-benzyl-8-azobicyclo[3.2.1]octan-3-exo-amine

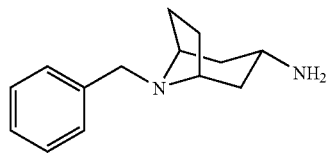

A solution of 8-benzylbicyclo[3.2.1.]octan-3-one-O-methyloxime (27.78 g) in pentanol (500 ml) was heated to 165° C. Sodium (10 g) was added portionwise over 6 hours. The reaction was heated for a further 4 hours and then cooled to 5° C. The reaction was acidified with 6M hydrochloric acid and the phases separated. The aqueous extracts were basified with sodium hydroxide and extracted with ethyl acetate (3×100 ml). The combined organic extracts were dried and evaporated to dryness to give the title compound as a pale brown oil. Yield 20.21 g. MS 217 MH+.

Step 4: Preparation of N-(8-benzyl-8-azabicyclo[3.2.1]oct-3-yl-exo)-2-methylpropanamide

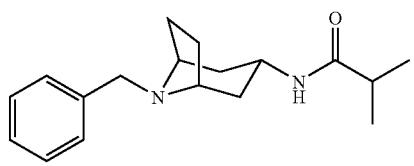

To a solution of 8-benzyl-8-azobicyclo[3.2.1]octan-3-exo-amine (10 g) in DMF (20 ml) was added triethylamine (9.7 ml) and isobutyric acid (6.43 ml) followed by O-(7-azabenzotriazol-1yl)-N,N,N'N'-tetramethyluronium hexafluorophosphate (HATU, 26.36 g) and the resulting mixture was allowed to stir for 18 hours. The reaction mixture was poured onto water and extracted with ethyl acetate (3×50 ml). The organics were extracted with 6M hydrochloric acid. The acid extracts were basified with sodium hydroxide and then extracted with ethyl acetae (3×50 ml). The organic extracts were dried and evaporated to dryness to give the title compound as a pale brown solid. Yield 5.99 g. MS 287 MH+; NMR CDCl$_3$ 1.1 (d, 6H), 1.5 (m, 2H), 1.6-2.05 (m, 6H), 2.3 (m, 1H), 3.2 (m, 2H), 4.2 (m, 1H), 5.2 (m, 1H), 7.2-7.4 (m, 5H).

Step 5: Preparation of 8-Benzyl-3-(3-isopropyl-5-methyl-4H-1,2,4-triazol-4-yl)-exo-8-azabicyclo[3.2.1]octane

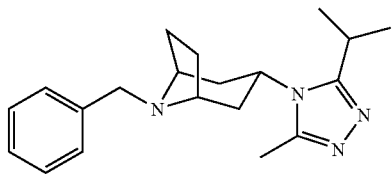

Phosphorous oxychloride (13 ml) was added slowly to a solution of N-(8-benzyl-8-azabicyclo[3.2.1]oct-3-yl-exo)-2-methylpropanamide (13.27 g) in pyridine (25 ml) and chloroform (50 ml) at 0° C. The reaction mixture was allowed to warm to room temperature and then allowed to stir for 18 hours. The mixture was evaporated and azeotroped with toluene. The residue was dissolved in chloroform (50 ml) and diisopropylethylamine (24 ml) and acetic anhydride (5.15 g) was added and the resulting mixture was refluxed for 18 hours. Saturated aqueous sodium carbonate (250 ml) was added and the product was extracted with dichloromethane. The organic extracts were dried and evaporated. The residue was dissolved in 6M hydrochloric acid and refluxed for 18 hours. The reaction mixture was allowed to cool to room temperature, basified with 6M sodium hydroxide, extracted with dichloromethane (3×50 ml), dried and evaporated to dryness. The residue was purified by column chromatography on silica eluting with a gradient of dichloromethane to 5% (7M NH$_3$ in methanol) in dichloromethane to give the title compound as an off white solid. Yield 2.31 g. MS 325 MH+. NMR CDCl$_3$ 1.4 (d, 6H), 1.7 (m, 4H), 2.1-2.4 (m, 4H), 2.6 (s, 3H), 3.05 (m, 1H), 3.4 (bs, 2H), 3.6 (s, 2H), 4.3 (m, 1H), 7.2-7.4 (m, 5H).

Step 6: Preparation of 3-(3-isopropyl-5-methyl-4H-1,2,4-triazolyl)-exo-8-azabicyclo[3.2.1]octane

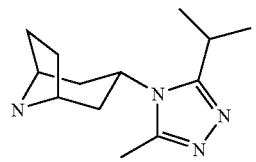

To a solution of 8-benzyl-3-(3-isopropyl-5-methyl-4H-1,2,4-triazol-4-yl)-exo-8-azabicyclo[3.2.1]octane (2.3 g) in ethanol (70 ml) was added 20% palladium hydroxide (230 mg) and the resulting mixture was stirred under a hydrogen atmosphere for 18 hours. The reaction mixture was filtered and evaporated to give the title compound as a white solid. Yield 1.88 g. NMR CDCl$_3$ 1.4(d, 6H), 1.7-1.8 (m, 4H), 1.95 (m, 2H), 2.1-2.3 (m, 4H), 2.55 (s, 3H), 3.05 (m, 1H), 4.35 (m, 1H).

Method X

Preparation of 1-endo-(8-azabicyclo[3.2.1]oct-3-yl)-5-(methylsufonyl)-1H-benzamidazole

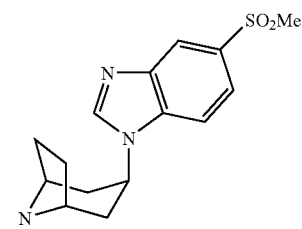

Step 1: Preparation of tert-butyl 3-oxo-8-azabicyclo[3.2.1]octane-8-carboxylate

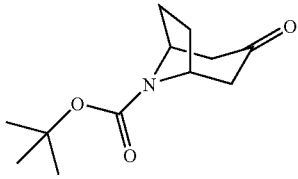

To a solution of 8-benzylbicyclo[3.2.1.]octan-3-one (8.48 g, Method W, step 1) in ethanol (100 ml) was added 30% palladium on carbon (850 mg) followed by ammonium formate (8.5 g) and the resulting mixture was refluxed for 4 hours. The mixture was cooled, filtered and evaporated to dryness. The residue was dissolved in ThF (50 ml) and water (50 ml) and d-tert-butyl dicarbonate (8.61 g) was added. The resulting mixture was stirred at room temperature for 18 hours. The reaction mixture was concentrated and then partitioned between dichloromethane and 1M citric acid. The organic extracts were washed with saturated sodium bicarbonate, brine, dried and evaporated to dryness. The residue was purified by chromatography on silica eluting with ethyl acetate/isohexane (20:80) to give the title compound as an oil which solidified on standing. Yield 4.43 g. NMR CDCl$_3$: 1.5 (s, 9H), 1.7 (m, 2H), 2.1 (m, 2H), 2.35 (m, 2H), 2.7 (m, 2H), 4.5 9m, 2H).

Step 2: Preparation of tert-butyl 3-endo-(benzylamino)-8-azabicyclo[3.2.1]octane-8-carboxylate

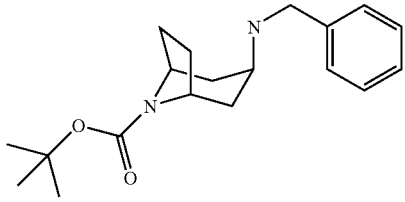

To a solution of of tert-butyl 3-oxo-8-azabicyclo[3.2.1]octane-8-carboxylate (4.43 g) in dichloromethane (90 ml) and acetic acid (10 ml) was added benzylamine (2.37 ml) followed by sodium triacetoxyborohydride (6.3 g) and the resulting mixture was stirred for 18 hours. The reaction mixture was concentrated, redissolved in ethyl acetate and washed with saturated sodium bicarbonate. The organic layers were dried and evaporated to dryness. The residue was purified by chromatography on silica eluting with a gradient of ethyl acetate/isohexane to give the title compound as a solid. Yield 2.84 g. NMR CDCl$_3$: 1.5 (s, 9H), 1.6 (m, 2H), 1.9-2.2 (m, 5H), 3.0 (m, 1H), 3.75 9s, 2H), 4.1 (m, 2H), 7.3 (m, 5H).

Step 3: Preparation of tert-butyl 3-endo-amino-8-azabicyclo[3.2.1]octane-8-carboxylate

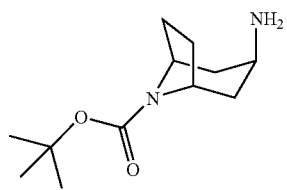

To a solution of tert-butyl 3-endo-(benzylamino)-8-azabicyclo[3.2.1]octane-8-carboxylate (2.84 g) in ethanol (50 ml) was added 30% palladium on carbon (286 mg) followed by ammonium formate (3 g) and the resulting mixture was refluxed for 2.5 hours. The mixture was cooled, filtered and evaporated to dryness to give the title compound, which was used without further purification. MS 227 MH$^+$.

Step 4: Preparation of tert-butyl 3-{[4-(methylsulfonyl)-2-nitrophenyl]amino}-8-endo-azabicyclo[3.2.1]octane-8-carboxylate.

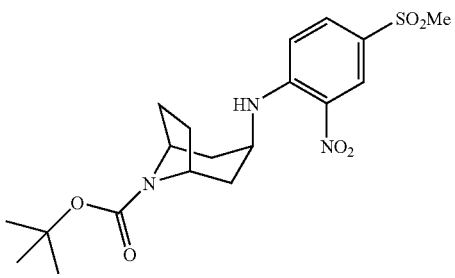

Prepared in a similar manner to Method A, step 1 but using of tert-butyl 3-endo-amino-8-azabicyclo[3.2.1]octane-8-carboxylate (2.12 g) to give the title compound as a foam. Yield 3.24 g. NMR CDCl$_3$: 1.5 (s, 9H), 1.8 (m, 2H), 2.0-2.2 (m, 6H), 3.1 (3, 3H), 4.0 (m, 1H), 4.3 (m, 2H), 6.85 (d, 1H), 7.9 (dd, 1H), 8.8 (d, 1H), 9.1 (d, 1H).

Step 5: Preparation of 1-endo-(8-azabicyclo[3.2.1]oct-3-yl)-5-(methylsufonyl)-1H-benzamidazole

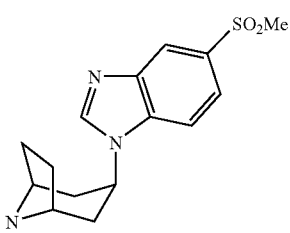

Step A: To a solution of tert-butyl 3-{[4-(methylsulfonyl)-2-nitrophenyl]amino}-8-endo-azabicyclo[3.2.1]octane-8-carboxylate (3.25 g) and trimethyl orthoformate (4.2 ml) in ethanol (100 ml) was added acetic acid (1 ml) and 10% palladium on carbon (100 mgl). The mixture was placed under an atmosphere of hydrogen (5 bar) and heated to 80° C. for 18 hours. The mixture was cooled and filtered to a gum.

Step B: The product form step A was dissolved in dioxane (20 ml) and 4M HCl (20 ml) was added. The resulting mixture was stirred for 1 hour. Diethyl ether (50 ml) was added and the mixture was filtered and washed with diethyl ether to give the title compound. MS 306 MH+.

Method Y

Preparation of 1-exo-(8-azabicyclo[3.2.1]oct-3-yl)-5-(methylsufonyl)-1H-benzamidazole

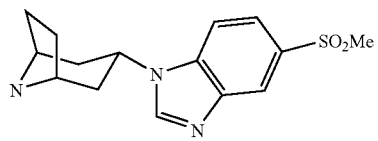

Step 1: Preparation of 8-benzyl-N-[4-(methylsulfonyl)-2-nitrophenyl]-8-exo-azabicyclo[3.2.1]octan-3-amine

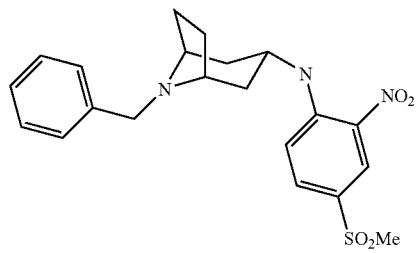

In a similar manner to Method A step 1 but using 8-benzyl-8-azobicyclo[3.2.1]octan-3-exo-amine (Method W step 3) was prepared 8-benzyl-N-[4-(methylsulfonyl)-2-nitrophenyl]-8-exo-azabicyclo[3.2.1]octan-3-amine. NMR CDCl$_3$: 1.8 (m, 4H), 2.1 (m, 2H), 2.3 (m, 2H), 3.15 (s, 3H), 3.45 (m, 2H), 3.7 (s, 2H), 4.0 (m, 1H), 7.1 (d, 1H), 7.4 (m, 4H), 7.95 (dd, 1H), 8.4 (d, 1H), 8.85 (d, 1H).

Step 2: Preparation of 1-(8-benzyl-8-exo-azabicyclo[3.2.1]oct-3-yl)-5-(methylsufonyl)-1H-benzamidazole

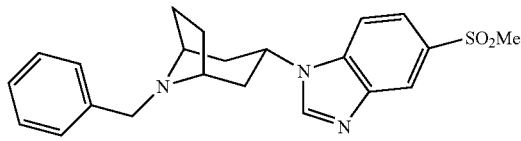

In a similar manner to Method X step 4 was prepared the title compound as oil, which solidified on standing. NMR CDCl$_3$: 1.9 (m, 4H), 2.3 (m, 4H), 3.1 (s, 3H), 3.45 (m, 2H), 3.65 (s, 2H), 4.7 (m, 1H), 7.4 (m, 5H), 7.65 (m, 1H), 7.9 (m, 1H), 8.2 (s, 1H), 8.4 (s, 1H).

Step 3: Preparation of 1-exo-(8-azabicyclo[3.2.1]oct-3-yl)-5-(methylsufonyl)-1H-benzamidazole To a solution of 1-(8-benzyl-8-exo-azabicyclo[3.2.1]oct-3-yl)-5-(methylsufonyl)-1H-benzamidazole (1.1 g) in ethanol (50 ml) was added 30% palladium on carbon (110 mg) followed by ammonium formate (1.1 g) and the resulting mixture was heated to 90° C. for 5 hours. An additional portion of ammonium formate (1.1 g) and 30% palladium on carbon (110 mgs) was added and the mixture was heated for a further 8 hours. The mixture was cooled, filtered and evaporated to give a gum, which was purified on a SCX column to give the title compound as a solid. Yield 750 mg. NMR CDCl$_3$: 1.8-2.3 (m, 8H), 3.1 (s, 3H), 3.8 (m, 2H), 4.7 (m, 1H), 7.6 (d, 1H), 7.9 (dd, 1H), 8.2 (s, 1H), 8.4 (s, 1H). MS 306 MH+.

EXAMPLE 3

The ability of compounds to inhibit the binding of MIP-1α was assessed by an in vitro radioligand binding assay. Membranes were prepared from Chinese hamster ovary cells which expressed the recombinant human CCR5 receptor. These membranes were incubated with 0.1 nM iodinated MIP-1α, scintillation proximity beads and various concentrations of the compounds of the invention in 96-well plates. The amount of iodinated MP-1α bound to the receptor was determined by scintillation counting. Competition curves were obtained for compounds and the concentration of compound which displaced 50% of bound iodinated MIP-1α was calculated (IC$_{50}$). Preferred compounds of formula (I) have an IC$_{50}$ of less than 50 µM.

Results from this test for certain compounds of the invention from Table I are presented in Table III. In Table III the results are presented as Pic50 values. A Pic50 value is the negative log (to base 10) of the IC$_{50}$ result, so an IC50 of 1 µm (that is 1×10$^{-6}$ M) gives a Pic50 of 6. If a compound was tested more than once then the data below is an average of the probative tests results.

TABLE III

| Compound No. | Pic50 |
|---|---|
| 1 | 9.0 |
| 2 | 7.4 |
| 3 | 8.9 |
| 4 | 7.8 |
| 5 | 8.4 |
| 6 | 7.2 |
| 7 | 8.0 |
| 8 | 8.0 |
| 9 | 7.7 |
| 10 | 7.7 |
| 11 | 9.0 |
| 12 | 7.7 |
| 13 | 6.8 |

SCHEME 1
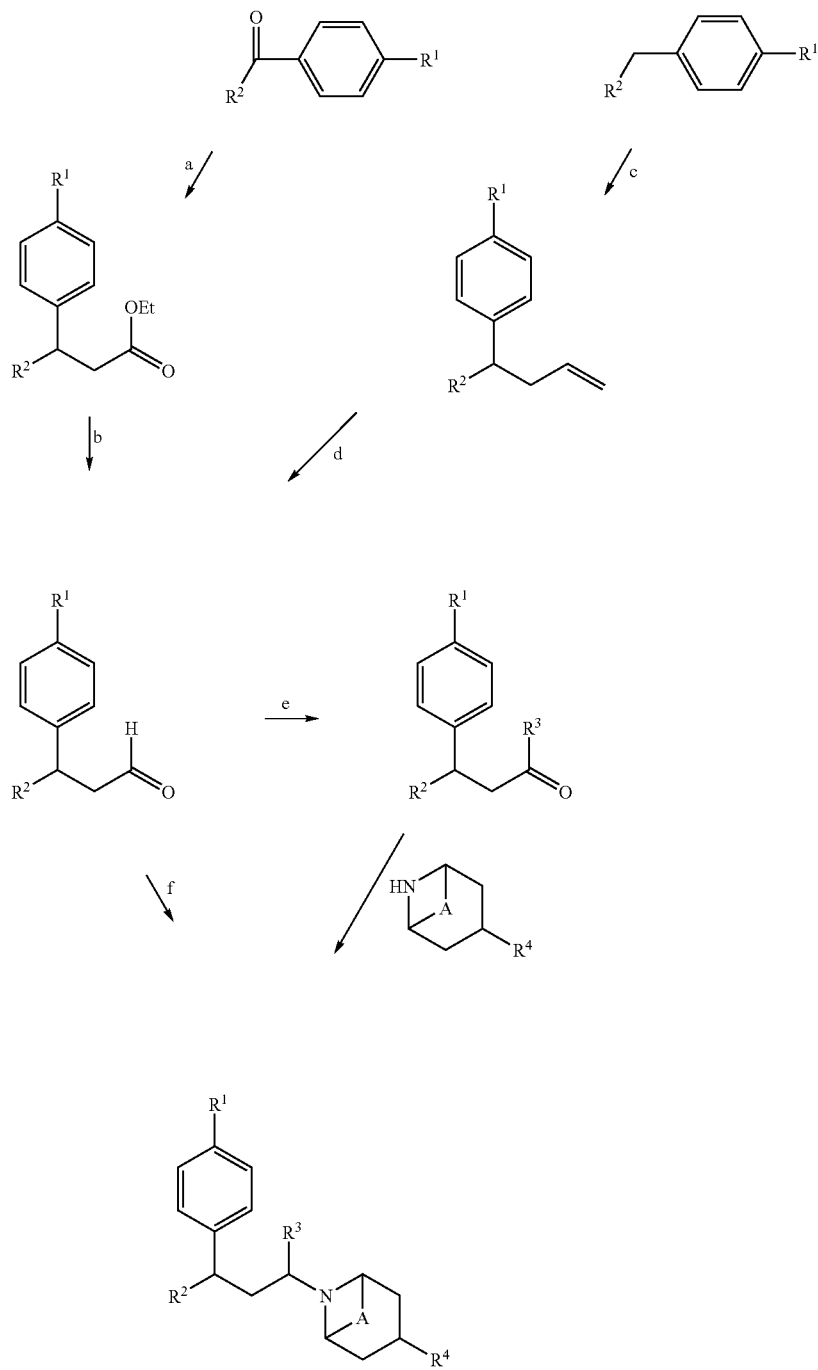
Conditions
a) (i) (EtO)$_2$P(=O)CH$_2$CO$_2$Et, base; (ii) hydrogenation (e.g. Pd(OH)$_2$, H$_2$)
b) (i) Reduction (e.g. LiAlH$_4$); (ii) Oxidation (e.g. Dess-Martin periodinane)
c) Allyl bromide, base (e.g. LDA)
d) O$_3$ then Me$_2$S
e) (i) R$^3$MgBr (ii) Oxidation
f) Reductive amination (NaBH(OAc)3, AcOH)

SCHEME 2

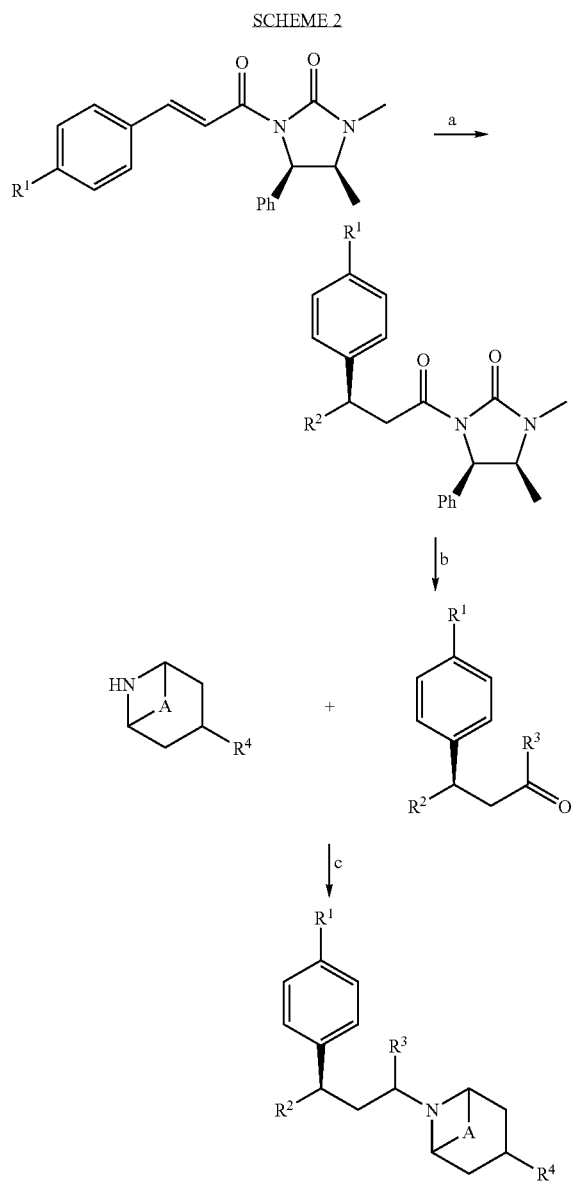

Conditions
a) R²MgBr, CuI, TMEDA, n-Bu₂BOTf
b) Reduction-oxidation (for when R³ is H), or Reduction-oxidation then R³MgBr (for when R³ is alkyl) then oxidation
c) Reductive amination (NaBH(OAc)₃, AcOH)

The invention claimed is:
1. A compound of formula (I):

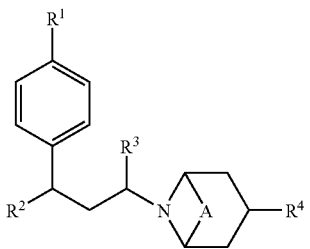

(I)

wherein:

A is absent or is $CH_2CH_2$;

$R^1$ is halo, hydroxy, nitro, $(CH_2)_nS(O)_k(C_{1-6}$ alkyl), $(CH_2)_nS(O)_2NH_2$, $(CH_2)_nS(O)_2NH(C_{1-6}$ alkyl), $(CH_2)_n S(O)_2NHCHO$, $(CH_2)_nS(O)_2N(C_{1-6}$ alkyl)$_2$, $OS(O)_2(C_{1-6}$ alkyl), cyano, $C_{1-6}$ alkyl, $C_{1-6}$ alkoxy, $NH_2$, $NH(C_{1-6}$ alkyl), $N(C_{1-6}$ alkyl)$_2$, $C(O)NH_2$, $C(O)NH(C_{1-6}$ alkyl), $C(O)N(C_{1-6}$ alkyl)$_2$, C(O)[N-linked heterocyclyl], $CO_2H$, $CO_2(C_{1-6}$ alkyl), $NHC(O)(C_{1-6}$ alkyl), $NHC(O)O(C_{1-6}$ alkyl), $(CH_2)_nNHS(O)_2(C_{1-6}$ alkyl), $C(O)(C_{1-6}$ alkyl), $CF_3$, $OCF_3$, phenyl, heteroaryl, $(C_{1-4}$ alkyl)phenyl, $(C_{1-4}$ alkyl)heteroaryl, NHC(O)phenyl, NHC(O)heteroaryl, $NHC(O)(C_{1-4}$ alkyl)phenyl, $NHC(O)(C_{1-4}$ alkyl)heteroaryl, $NHS(O)_2$ phenyl, $NHS(O)_2$ heteroaryl, $NHS(O)_2(C_{1-4}$ alkyl)phenyl, $NHS(O)_2(C_{1-4}$ alkyl)heteroaryl, $NHC(O)NH(C_{1-6}$ alkyl), $NHC(O)NH(C_{3-7}$ cycloalkyl), NHC(O)NHphenyl, NHC(O)NHheteroaryl, $NHC(O)NH(C_{1-4}$ alkyl)phenyl or $NHC(O)NH(C_{1-4}$ alkyl)heteroaryl; wherein the foregoing phenyl and heteroaryl groups are optionally substituted by halo, hydroxy, nitro, $S(O)_m(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

$R^2$ is phenyl, halophenyl, thienyl or halothienyl;

$R^3$ is hydrogen or methyl;

$R^4$ is a five membered heterocycle containing at least one carbon atom, one to four nitrogen atoms and, optionally, one oxygen or sulphur atom, said heterocycle being optionally substituted by oxo, $C_{1-6}$ alkyl, $H_2NC(O)$, (phenyl$C_{1-2}$ alkyl)HNC(O), $C_{1-2}$ alkyl(phenyl) [which is optionally substituted by halogen, $C_{1-4}$ alkyl, $C_{1-4}$ alkoxy, $CF_3$, $OCF_3$, $S(C_{1-4}$ alkyl), $S(O)(C_{1-4}$ alkyl) or $S(O)_2(C_{1-4}$ alkyl)], $S(C_{1-4}$ alkyl), $S(C_{1-2}$ alkyl(phenyl)), $NH_2$ or phenyl; the five membered heterocycle being optionally fused to a cyclohexane, piperidine, benzene, pyridine, pyridazine, pyrimidine or pyrazine ring; the ring carbon atoms of said fused cyclohexane, piperidine, benzene, pyridine, pyridazine, pyrimidine or pyrazine ring being optionally substituted by halogen, cyano, $C_{1-4}$ alkyl, $C_{1-4}$ alkoxy, $CF_3$, $OCF_3$, $NH_2$, $S(C_{1-4}$ alkyl), $S(O)(C_{1-4}$ alkyl) or $S(O)_2(C_{1-4}$ alkyl); and the nitrogen of the fused piperidine ring being optionally substituted by $C_{1-4}$ alkyl {which is optionally substituted by oxo, halogen, OH, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl)$_2$, $NH_2$, $NH(C_{1-4}$ alkyl) or $N(C_{1-4}$ alkyl)$_2$}, $C(O)(C_{1-4}$ alkyl) {wherein the alkyl is optionally substituted by $C_{1-4}$ alkoxy or fluoro}, $C(O)O(C_{1-4}$ alkyl), $C(O)NH_2$, $C(O)NH(C_{1-4}$ alkyl), $C(O)N(C_{1-4}$ alkyl)$_2$ or $S(O)_2(C_{1-4}$ alkyl) {wherein the alkyl is optionally substituted by fluoro};

k, m and n are, independently, 0, 1 or 2;

or a pharmaceutically acceptable salt thereof.

2. A compound of formula (I) as claimed in claim 1 wherein A is absent.

3. A compound of formula (I) as claimed in claim 1 wherein $R^1$ is halo, cyano, $S(O)_2(C_{1-6}$ alkyl), $OS(O)_2(C_{1-6}$ alkyl), $CO_2(C_{1-6}$ alkyl), $NHC(O)(C_{1-6}$ alkyl), $NHS(O)_2(C_{1-6}$ alkyl), NHC(O)phenyl, NHC(O)heteroaryl, $NHC(O)(C_{1-4}$ alkyl)phenyl, $NHC(O)(C_{1-4}$ alkyl)heteroaryl, $NHS(O)_2$phenyl, $NHS(O)_2$heteroaryl, $NHS(O)_2(C_{1-4}$ alkyl)phenyl or $NHS(O)_2(C_{1-4}$ alkyl)heteroaryl; wherein the foregoing phenyl and heteroaryl groups are optionally substituted by halo, hydroxy, nitro, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$.

4. A compound of formula (I) as claimed in claim 1 wherein $R^1$ is halo, cyano, $S(O)_2(C_{1-6}$ alkyl), $OS(O)_2(C_{1-6}$ alkyl), $CO_2(C_{1-6}$ alkyl), $NHC(O)(C_{1-6}$ alkyl) or $NHS(O)_2(C_{1-6}$ alkyl).

5. A compound of formula (I) as claimed in claim 1 wherein $R^2$ is phenyl or halophenyl.

6. A compound of formula (I) as claimed in claim 1 wherein $R^3$ is hydrogen.

7. A compound of formula (I) as claimed in claim 1 wherein $R^4$ is imidazolyl, 1,2,4-triazolyl, 1,2,4-oxadiazolyl, tetrazolyl, pyrazolyl, 1,3-thiazolyl, or isoxazolyl optionally substituted as described in claim 1.

8. A process for preparing a compound of formula (I) as claimed in claim 1, the process comprising reductive amination of a compound of formula (II):

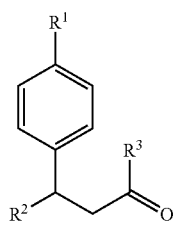

(II)

with a compound of formula (III):

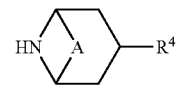

(III)

in the presence of $NaBH(OAc)_3$ (wherein Ac is $C(O)CH_3$) and acetic acid, in a suitable solvent at room temperature.

9. A pharmaceutical composition which comprises a therapeutically effective amount of a compound as claimed in claim 1, or a pharmaceutically acceptable salt thereof, and a pharmaceutically acceptable adjuvant, diluent or carrier.

10. A compound as claimed in claim 2 wherein $R^1$ is halo, cyano, $S(O)_2(C_{1-6}$ alkyl), $OS(O)_2(C_{1-6}$ alkyl), $CO_2(C_{1-6}$ alkyl), $NHC(O)(C_{1-6}$ alkyl), $NHS(O)_2(C_{1-6}$ alkyl), NHC(O)phenyl, NHC(O)heteroaryl, $NHC(O)(C_{1-4}$ alkyl)phenyl, $NHC(O)(C_{1-4}$ alkyl)heteroaryl, $NHS(O)_2$phenyl, $NHS(O)_2$heteroaryl, $NHS(O)_2(C_{1-4}$ alkyl)phenyl or $NHS(O)_2(C_{1-4}$ alkyl)heteroaryl; wherein the foregoing phenyl and heteroaryl groups are optionally substituted by halo, hydroxy, nitro, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$.

11. A compound as claimed in claim 2 wherein $R^1$ is halo, cyano, $S(O)_2(C_{1-6}$ alkyl), $OS(O)_2(C_{1-6}$ alkyl), $CO_2(C_{1-6}$ alkyl), $NHC(O)(C_{1-6}$ alkyl) or $NHS(O)_2(C_{1-6}$ alkyl).

12. A compound as claimed in claim 2 wherein $R^2$ is phenyl or halophenyl.

13. A compound as claimed in claim 2 wherein $R^3$ is hydrogen.

14. A compound as claimed in claim 2 wherein $R^4$ is imidazolyl, 1,2,4-triazolyl, 1,2,4-oxadiazolyl, tetrazolyl, pyrazolyl, 1,3-thiazolyl, or isoxazolyl optionally substituted as described in claim 1.

15. A compound as claimed in claim 3 wherein $R^2$ is phenyl or halophenyl.

16. A compound as claimed in claim 3 wherein $R^3$ is hydrogen.

17. A compound as claimed in claim 3 wherein $R^4$ is imidazolyl, 1,2,4-triazolyl, 1,2,4-oxadiazolyl, tetrazolyl, pyrazolyl, 1,3-thiazolyl, or isoxazolyl optionally substituted as described in claim 1.

* * * * *